US009645291B1

(12) United States Patent
Sommer et al.

(10) Patent No.: US 9,645,291 B1
(45) Date of Patent: May 9, 2017

(54) VOLTAGE-TUNABLE OPTICAL FILTERS FOR INSTRUMENTATION APPLICATIONS

(71) Applicant: II-VI Incorporated, Saxonburg, PA (US)

(72) Inventors: Thomas Radford Sommer, Sebastopol, CA (US); William Kastanis, Santa Rosa, CA (US)

(73) Assignee: II-VI Incorporated, Saxonburg, PA (US)

( * ) Notice: Subject to any disclaimer, the term of this patent is extended or adjusted under 35 U.S.C. 154(b) by 0 days.

(21) Appl. No.: 15/131,249

(22) Filed: Apr. 18, 2016

(51) Int. Cl.
| | |
|---|---|
| *G01N 21/64* | (2006.01) |
| *G02B 5/20* | (2006.01) |
| *G02B 21/16* | (2006.01) |
| *G02B 21/06* | (2006.01) |
| *G01J 3/44* | (2006.01) |
| *G01J 3/12* | (2006.01) |
| *G02B 21/00* | (2006.01) |
| *G02B 5/00* | (2006.01) |

(52) U.S. Cl.
CPC ............. *G02B 5/204* (2013.01); *G01J 3/12* (2013.01); *G01J 3/44* (2013.01); *G02B 5/008* (2013.01); *G02B 5/207* (2013.01); *G02B 21/0064* (2013.01); *G02B 21/06* (2013.01); *G02B 21/16* (2013.01); *G01J 2003/1213* (2013.01)

(58) Field of Classification Search
CPC .............................. G02B 11/002; G02B 5/284
See application file for complete search history.

(56) References Cited

U.S. PATENT DOCUMENTS

| | | |
|---|---|---|
| 4,791,310 A | 12/1988 | Honig et al. |
| 5,591,981 A | 1/1997 | Heffelfinger et al. |
| (Continued) | | |

FOREIGN PATENT DOCUMENTS

DE    19835070 A1 *  2/2000  .......... G02B 21/002

OTHER PUBLICATIONS

M. Lequime, "Tunable thin-film filters: review and perspectives," 2004, Proceedings of SPIE, vol. 5250, pp. 302-311.*

(Continued)

*Primary Examiner* — Kiho Kim
(74) *Attorney, Agent, or Firm* — Wendy W. Koba

(57) ABSTRACT

A series combination of a shortwave pass (SWP) filter and a longwave pass (LWP) filter is provided in an arrangement where the filters are separately and independently controlled by voltages applied to the respective filters. The applied voltages modify the response profile of the associated filters, where changes in the voltage applied to the SWP filter changes its cut-off wavelength $\lambda_S$ and changes in the voltage applied to the LWP filter changes its cut-on wavelength $\lambda_L$ (the bandwidth of the combined arrangement between the span between $\lambda_L$ and $\lambda_S$). The ability to independently tune both the SWP and LWP filters allows for the combined result of their series combination to modify both the center wavelength (CWL) and bandwidth (BW) of the overall filter resulting from their combination.

38 Claims, 24 Drawing Sheets

(56) References Cited

U.S. PATENT DOCUMENTS

| | | |
|---|---|---|
| 6,867,899 B2 | 3/2005 | Knebel |
| 7,030,989 B2 | 4/2006 | Yager et al. |
| 7,180,602 B2 | 2/2007 | Riza et al. |
| 7,285,787 B2 | 10/2007 | Horigome et al. |
| 7,298,428 B1 | 11/2007 | Yuan et al. |
| 7,826,055 B2 | 11/2010 | Scobey et al. |
| 8,274,739 B2 | 9/2012 | Lee et al. |
| 8,441,710 B2 | 5/2013 | Wang et al. |
| 8,462,420 B2 | 6/2013 | Lee et al. |
| 8,550,681 B2 | 10/2013 | Sommer et al. |
| 2004/0234198 A1 | 11/2004 | Wagner et al. |
| 2006/0256338 A1* | 11/2006 | Gratton ............ G01N 15/1463 356/417 |
| 2007/0290145 A1* | 12/2007 | Viellerobe ........... A61B 5/0062 250/459.1 |
| 2009/0080194 A1 | 3/2009 | Bouzid et al. |
| 2009/0218513 A1* | 9/2009 | Bec .................. G01N 21/6452 250/458.1 |
| 2013/0329270 A1 | 12/2013 | Nielsen et al. |
| 2013/0342674 A1* | 12/2013 | Dixon ................... G02B 21/36 348/79 |
| 2014/0125990 A1* | 5/2014 | Hinderling ............ G02B 5/284 356/496 |
| 2014/0185054 A1* | 7/2014 | Atia ................... G01B 9/02004 356/479 |

OTHER PUBLICATIONS

Czajkowski, et al., "Optical Filtering Basics for Life Sciences", BioOptics World, Dec. 2015, pp. 53-56.

Alluxa Engineering Staff, "Next Generation Thin Film Optical Filters for Life Sciences", Alluxa, White Paper Series, Sep. 2012.

Favreau, et al., "Thin-Film Tunable Filters for Hyperspectral Fluorescence Microscopy", Journal of Biomedical Optics, Jan. 2014, vol. 19(1), pp. 011017-1 to 011017-11.

* cited by examiner

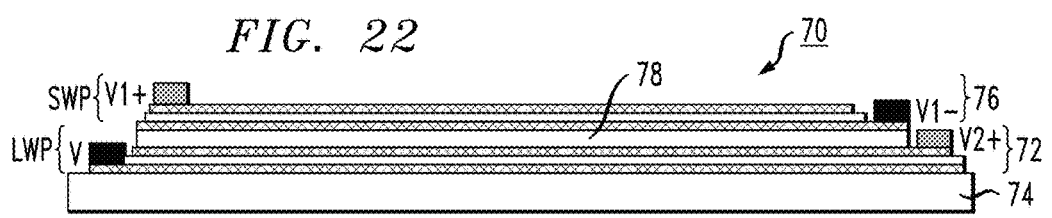
FIG. 22
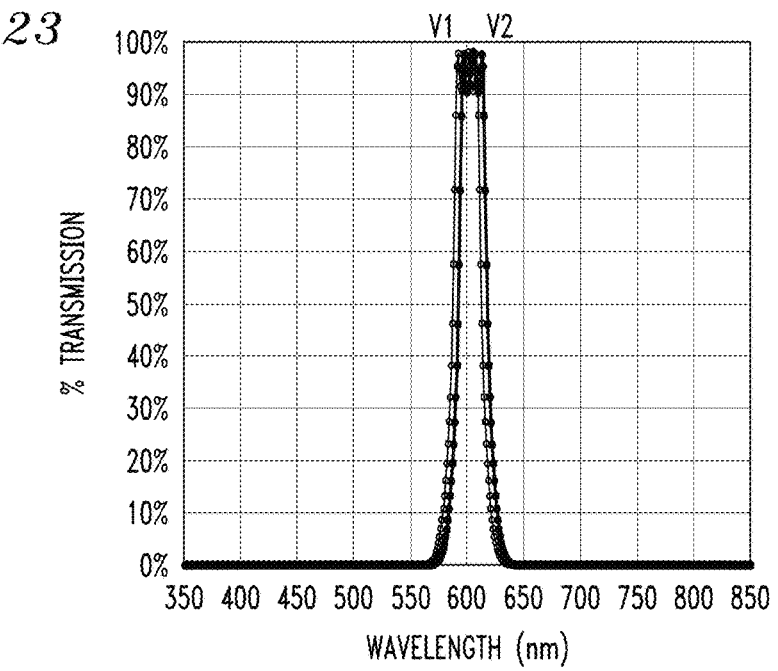
FIG. 23 (a)
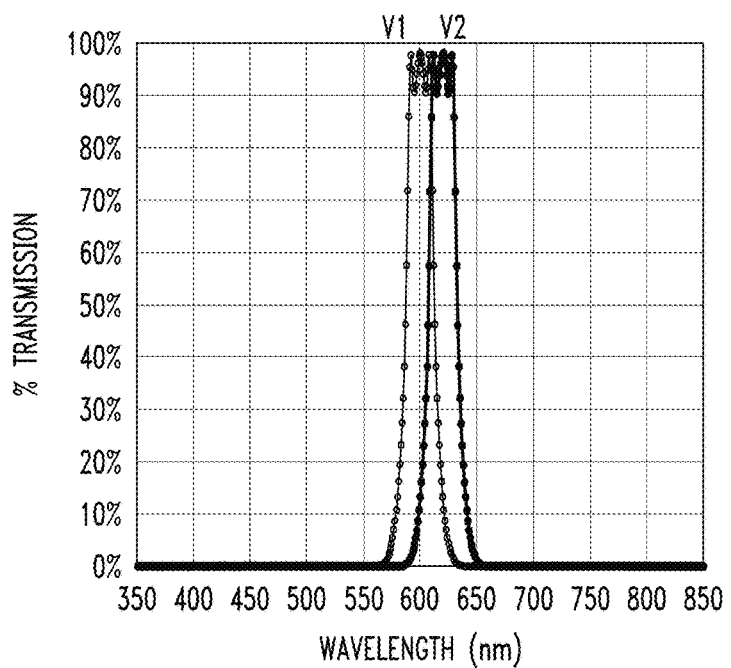
(B)

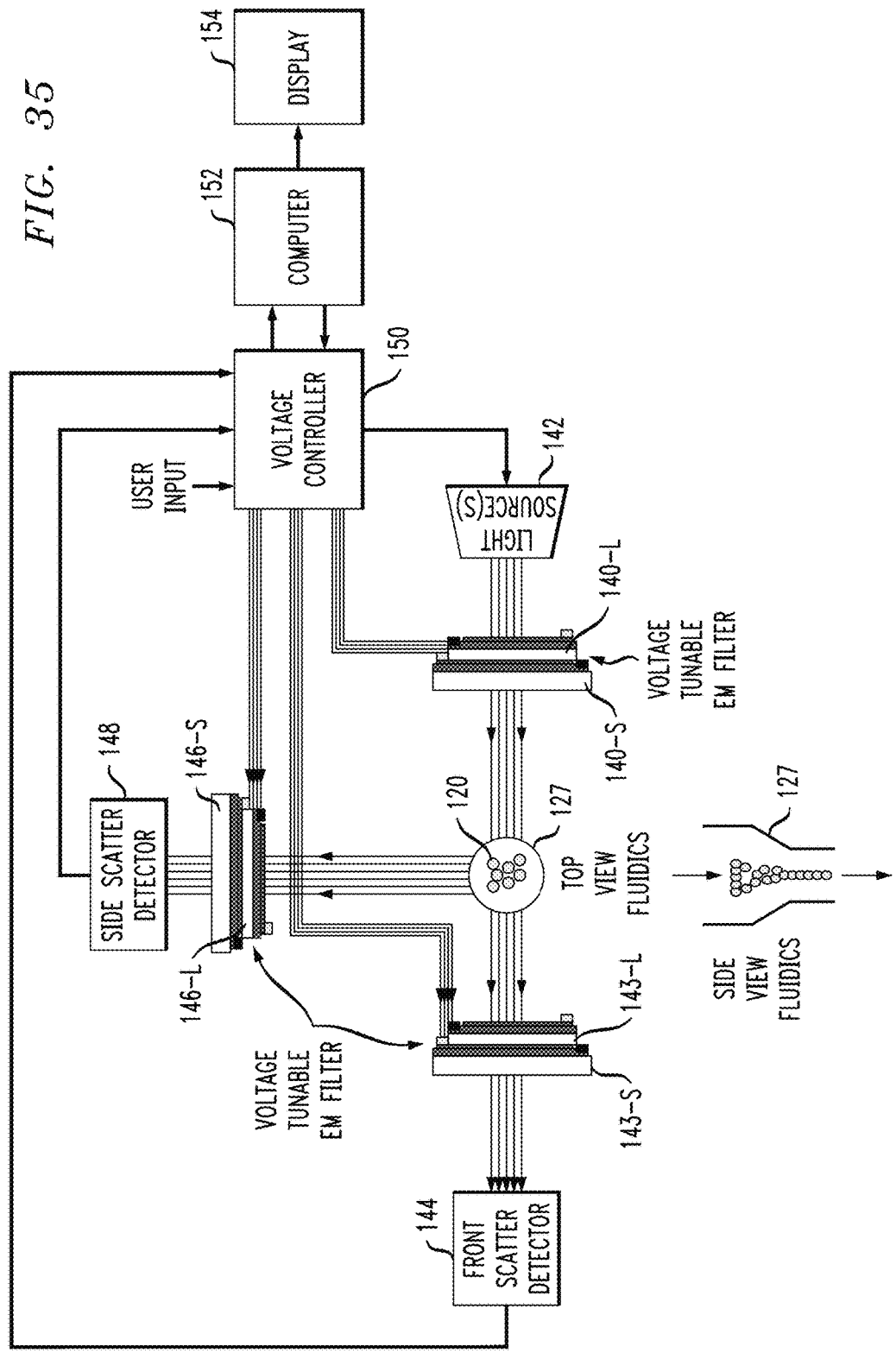

VOLTAGE-TUNABLE OPTICAL FILTERS FOR INSTRUMENTATION APPLICATIONS

TECHNICAL FIELD

The present invention relates to optical filters used in instrumentation applications and, more particularly, to a voltage-tunable optical filter that is variable in both center wavelength and bandwidth, and able to provide real-time changes to filter responses for various instrumentation applications (e.g., fluorescence spectrometry, Raman spectrometry, flow cytometry, etc.).

BACKGROUND OF THE INVENTION

Fluorescence microscopy typically involves the use of three separate optical filters: an excitation filter used to select an appropriate wavelength from the system illumination source, an emission filter to limit the fluorescence wavelength spectrum received at a detector from an illuminated specimen, and a dichroic filter positioned between both the excitation filter and the specimen, as well as the specimen and emission filter. The dichroic filter is used to separate the excitation wavelength band from the emission wavelength band. Raman spectroscopy uses a similar combination of filters (excitation, emission and dichroic). Flow cytometry utilizes a larger number of separate emission filters for extracting specific wavelength-based information from a "flow" of cells passing through the instrumentation.

It has been recognized that the filter components of these imaging systems are an enabling factor in advancing the state of the art with respect to obtaining accurate results. In particular, hyperspectral fluorescence microscopy now provides for signal collection over many different spectral bands, producing a contiguous spectrum output. Unlike traditional spectroscopy, however, hyperspectral microscopy requires the use of a variety of different filters. Prior art techniques combine elements such as gratings and prisms with mechanically tunable filters to provide the required bandwidth characteristics. Problems with signal loss remain. The need to utilize a large number of separate filters with flow cytometry has the same concerns.

Current attempts at creating tunable optical filters for these purposes involve mechanical configurations, such as motors and MEMS devices. As such, limitations associated with, for example, movable parts, angular displacement between elements and the like result in relatively slow response times (with respect to initiating the mechanical action to implement wavelength tuning), limiting the useful applications of these mechanical configurations. Tunable filters based on acousto-optic configurations have also been developed, but are known to also be relatively slow and bulky and, moreover, are typically limited in the wavelength range across which the tuning may be performed.

Thus, a need remains in the art for a tunable optical filter that exhibits a relatively fast response time while also providing a wide tuning range as needed for a variety of different applications.

SUMMARY

The need remaining in the prior art is addressed by the present invention, which relates to optical filters used in instrumentation applications and, more particularly, to a voltage-tunable optical filter that is independently variable in both center wavelength and bandwidth, and able to provide real-time, high speed changes to filter responses for various instrumentation applications (e.g., fluorescence spectrometry, Raman spectrometry, flow cytometry, etc.).

In accordance with one embodiment of the present invention, a series combination of a shortwave pass (SWP) filter and a longwave pass (LWP) filter is provided in an arrangement where the filters are separately and independently controlled by voltages applied to the respective filters. The applied voltages modify the response profile of the associated filters, where changes in a given applied voltage change the response for the associated filter. The ability to independently tune both the SWP and LWP filters allows for the combined result of their series combination to modify both the center wavelength (CWL) and bandwidth (BW) of the overall filter resulting from their combination.

In one embodiment, the inventive voltage-tunable filter is utilized as the excitation filter in a fluorescence spectroscopy system. In this embodiment, the voltages applied to the SWP and LWP filters can be controlled to provide a relatively narrow bandwidth filter response, with a CWL that is tunable over a wide spectral range (for example, over three octaves in the IR regime, e.g., tunable from 8 µm to 32 µm). This capability to change the CWL of the excitation filter simplifies the ability of the user to change the specific dye being evaluated (or optimize the measurement capabilities with the existing dye), as well as provide for the utilization of hyperspectral excitation, without the need to physically change the filter components (e.g., by using a "filter wheel"), as required by the prior art.

In another embodiment, the inventive voltage-tunable optical filter is utilized as the emission filter in a fluorescence spectroscopy system. In this embodiment, the voltage-controlled SWP and LWP filters are adjusted to change the CWL and BW of the response so as to find the wavelength range associated with the largest output power received at the instrument's detector (i.e., maximum signal emitted from the specimen).

In yet another embodiment, the inventive voltage-tunable optical filter is used as a dichroic filter that functions to help further separate the excitation wavelengths from the emission wavelengths, maintaining the separation as the characteristics of one or both of the excitation and emission CWLs and BWs are varied.

Other embodiments utilize combinations of voltage-tunable optical filters for two or more of the specific filters included in these systems.

Various other instrumentations that benefit from the utilization of the inventive filter arrangements include Raman spectrometers, flow cytometers, and the like.

One specific embodiment of the present invention takes the form of a voltage-controlled tunable optical filter comprising a shortwave pass (SWP) filter defined as exhibiting a selected cut-off wavelength $\lambda_S$ and a longwave pass (LWP) filter defined as exhibiting a selected cut-on wavelength $\lambda_L$, with $\lambda_L$ less than $\lambda_S$, wherein at least one of the SWP filter and the LWP filter has a voltage-controlled spectral response such that the combination of the SWP and LWP filters creates a tunable optical filter defined by the wavelength range between the cut-on wavelength $\lambda_L$ and the cut-off wavelength $\lambda_S$, providing a tunable center wavelength and an independently tunable bandwidth, depending on the selected values for $\lambda_L$ and $\lambda_S$.

Another specific embodiment of the present invention may be defined as an optical-based imaging system including at least one voltage-controlled tunable optical filter, with the system including a shortwave pass (SWP) filter defined as exhibiting a selected cut-off wavelength $\lambda_S$ and a longwave pass (LWP) filter defined as exhibiting a selected cut-on wavelength $\lambda_L$, with $\lambda_L$ less than $\lambda_S$, wherein at least one of the SWP filter and the LWP filter exhibits a voltage-controlled spectral response such that the combination of the SWP and LWP filters creates a tunable optical filter defined by the wavelength range between the cut-on wavelength $\lambda_L$ and the cut-off wavelength $\lambda_S$, providing a tunable center wavelength and an independently tunable bandwidth, depending on the selected values for $\lambda_L$ and $\lambda_S$.

Yet another particular embodiment of the present invention comprises voltage-controlled plasmonic tunable optical filter comprising a shortwave pass (SWP) plasmonic filter defined as exhibiting a selected cut-off wavelength $\lambda_S$ and a longwave pass (LWP) plasmonic filter defined as exhibiting a selected cut-on wavelength $\lambda_L$, with $\lambda_L$ less than $\lambda_S$, wherein at least one of the SWP plasmonic filter and the LWP plasmonic filter exhibits a voltage-controlled spectral response such that the combination of the SWP and LWP plasmonic filters creates a tunable optical filter defined by the wavelength range between the cut-on wavelength $\lambda_L$ and the cut-off wavelength $\lambda_S$, providing a tunable center wavelength and an independently tunable bandwidth, depending on the selected values for $\lambda_L$ and $\lambda_S$.

Other and further aspects and embodiments of the present invention will become apparent during the course of the following discussion and by reference to the accompanying drawings.

BRIEF DESCRIPTION OF THE DRAWINGS

Referring now to the drawings, where like numerals represent like parts in several views:

FIG. 22 illustrates a particular combination of a pair of filters formed as shown in FIG. 18 to create a voltage-controlled tunable optical filter for use as an excitation filter or an emission filter in a fluorescence spectrometer;

FIG. 23 shows a pair of different spectral responses for the filter combination of FIG. 22 under different circumstances, where graph (a) is associated with a condition where the applied voltages are relatively similar (with a large overlap in responses), and graph (b) is associated with a condition where the applied voltages are dissimilar (with a minimal overlap in responses);

FIG. 35 illustrates an exemplary flow cytometer formed using voltage-controlled tunable optical fibers, based on the diagram of FIG. 34.

DETAILED DESCRIPTION

Figure 1:
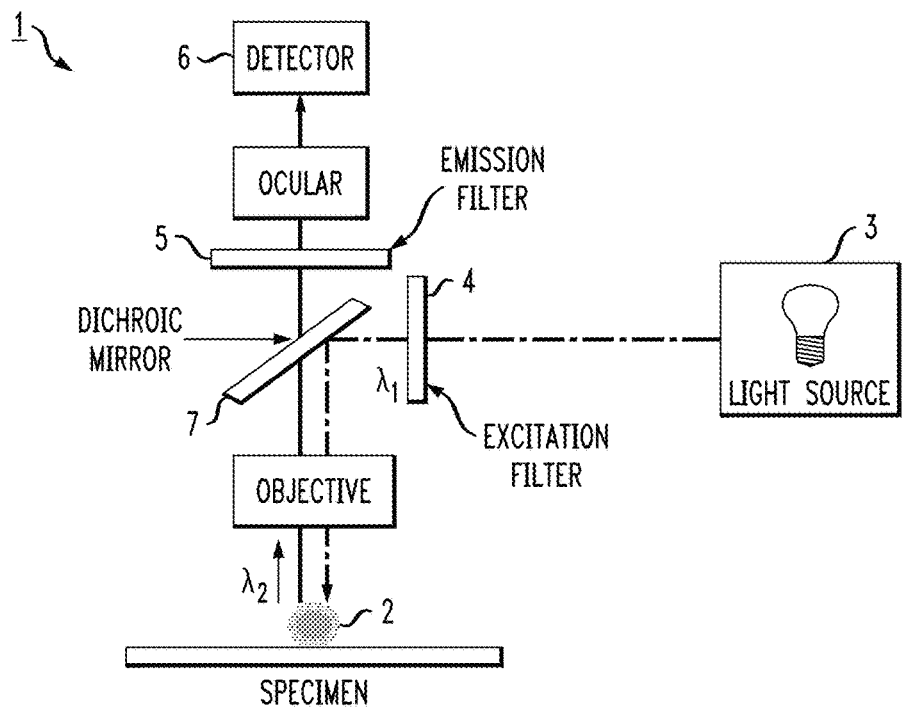
FIG. 1 depicts a prior art fluorescence microscopy system.

As will be discussed in detail below, there are a variety of different applications for a tunable optical filter in fluorescence-based imaging systems. FIG. 1 illustrates an exemplary prior art epifluorescence microscope 1 that benefits from the utilization of the inventive voltage-controlled tunable optical filter. Fluorescence microscopy provides magnified images of tissues, cells or other components of a specimen, using light emission for a plurality of fluorescent dyes that can be attached to specific components or features of the specimen. Referring to FIG. 1, a specimen 2 is prepared using one or more known fluorescent dyes (such as DAPI, GFP, RFP, YFP, an Alexa dye, Cy2, Cy3, Atto 488, fluorescein, etc.). A broadband light source 3 is used to illuminate specimen 2. As shown, the broadband output from light source 3 is first passed through an excitation filter 4 that is configured to pass only the specific wavelength range (denoted $\lambda_1$) that interacts with the specific dye being used to "excite" the specimen.

In response to the excitation, the specimen emits an optical signal within a second wavelength range (denoted $\lambda_2$) that passes through an emission filter 5 and is ultimately directed into a detector 6 used for analyzing the results of the microscopy. In most conventional arrangements, a dichroic filter 7 (also referred to at times as a "dichroic mirror") is used to direct the signals operating at $\lambda_1$ and $\lambda_2$ in the proper directions. That is, dichroic filter 7 "reflects" the bandwidth range around $\lambda_1$ (i.e., re-directs this signal toward the specimen), and "transmits" the bandwidth range around $\lambda_2$ (i.e., passes this signal toward the detector).

Oftentimes, the combination of the three filters (excitation, emission, and dichroic) are housed in a cube-like structure and sold as a stand-alone component. At times, this component is referred to as a "filter cube". Similar filter cubes may be used with Raman spectrometers.

Figure 2:
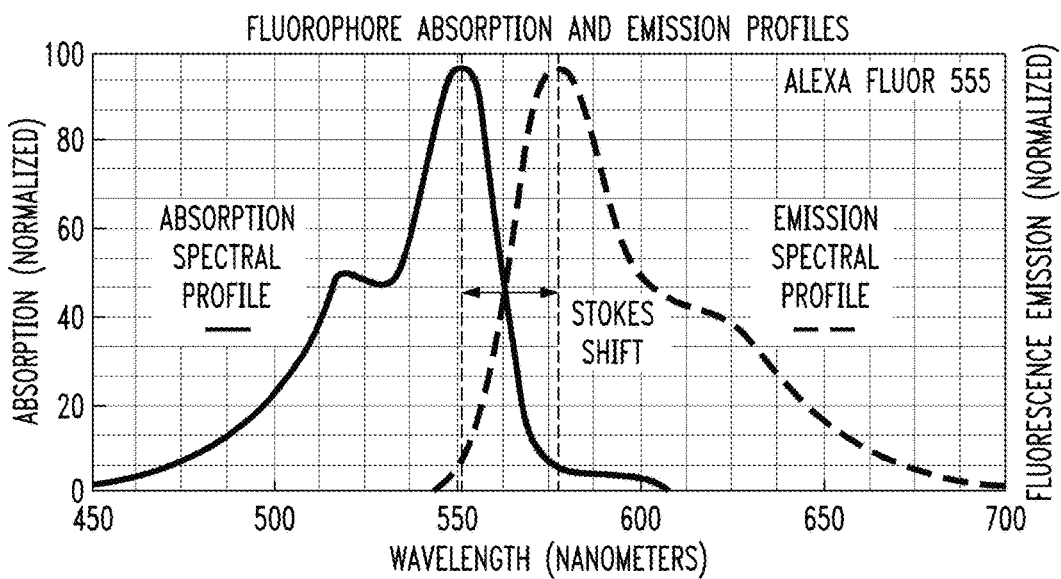
FIG. 2 illustrates the absorption and emission spectral profiles associated with a specific dye (Alexa Fluor 555)
Figure 3:
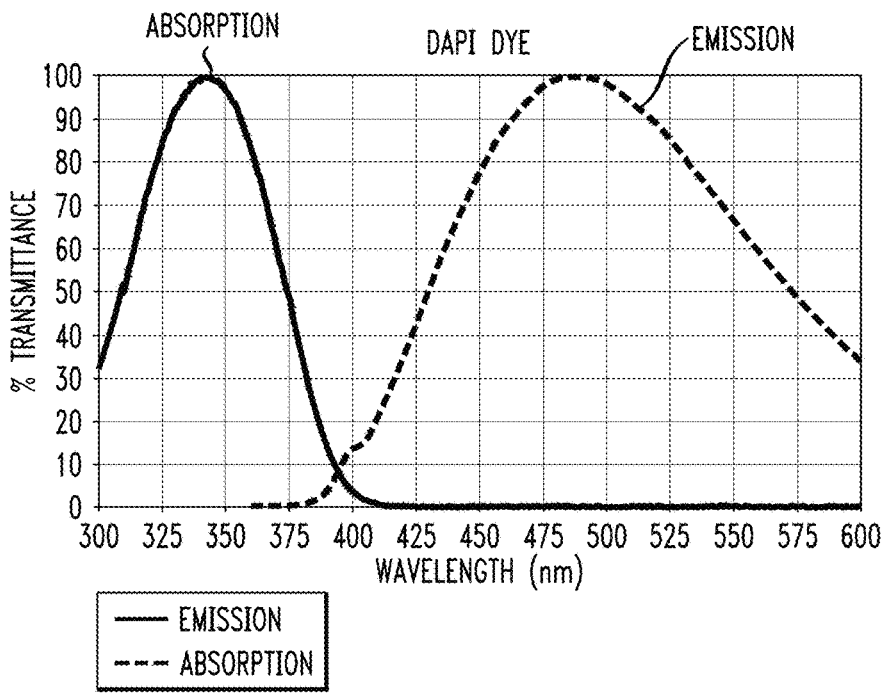
FIG. 3 illustrates the absorption and emission spectral profiles associated with a different dye (DAPI)
Figure 4:
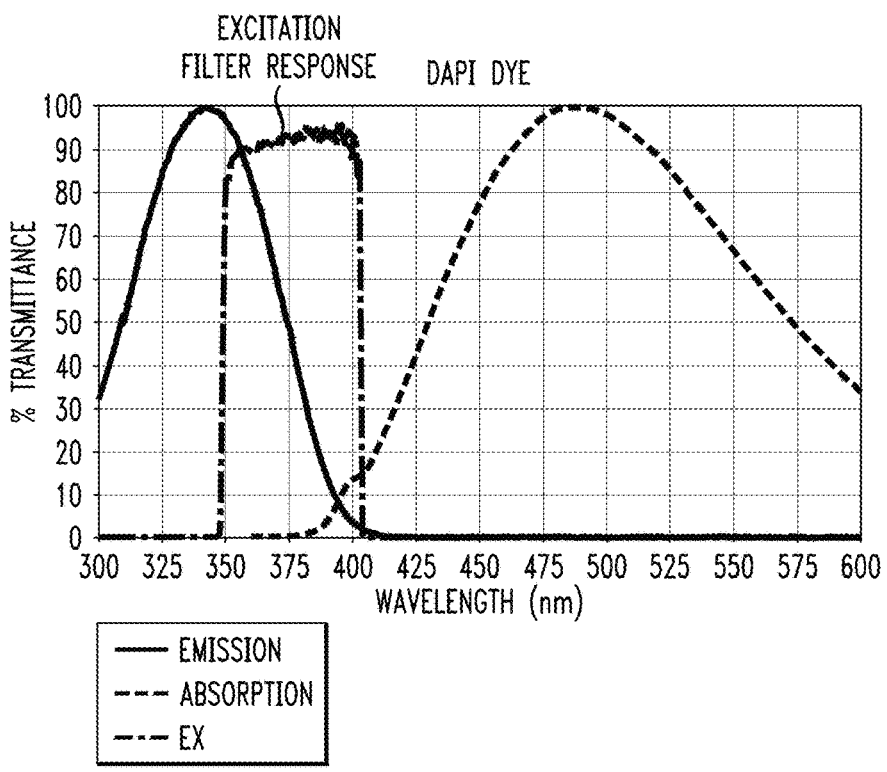
FIG. 4 is a graph depicting the absorption and emission spectral profiles as shown in FIG. 3, as well as a spectral response for a conventional excitation filter utilized in fluorescence spectrometers.

As mentioned above, one problem with expanding the utilization of fluorescence microscopy (particularly hyperspectral fluorescence microscopy) is the difficulty experienced in adjusting the wavelengths associated with these filters, particularly in situations where multiple dyes are used (each dye responding to a different wavelength). FIG. 2 illustrates the absorption and emission spectral profiles associated with one specific dye (Alexa Fluor 555). The absorption and emission spectral profiles associated with another specific dye (DAPI fluorophore) are shown in FIG. 3. Clearly, excitation and emission filters of different bandwidths are required to properly interact with the spectral profiles of the Alexa dye when compared to the DAPI dye. FIG. 4 contains the same absorption and emission spectral profiles as shown in FIG. 3, in this case also illustrating an exemplary filter response for a conventional excitation filter (shown as filter 4 in FIG. 1) for use with a DAPI dye fluorescence system. Here, the excitation filter is shown as taking the form of a bandpass filter having a pass band between about 350 nm and 400 nm is shown. While this filter response is useful in a system utilizing DAPI dye, the same filter cannot be used with the Alexa dye. Given the extensive number of different dyes that may be used, the problems associated with different filter characteristics becomes quite burdensome.

Figure 5:
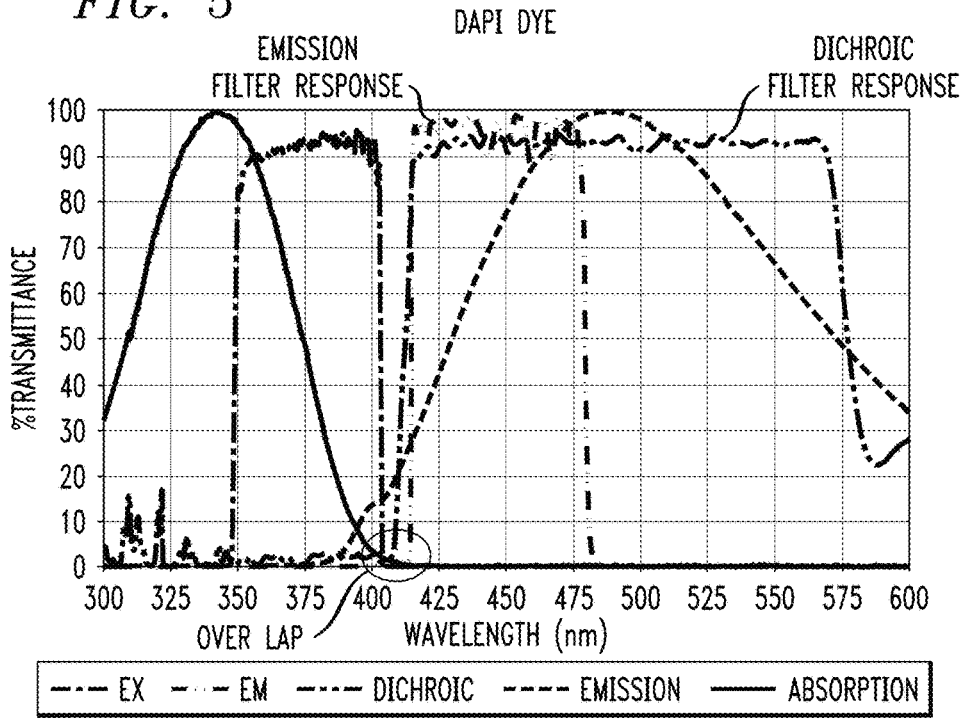
FIG. 5 is a graph that shows the same responses as shown in FIG. 4, as well as the spectral profiles for a dichroic filter and an emission filter, as found in fluorescence spectrometers.

FIG. 5 shows the various spectral profiles presented in FIG. 4, in addition to the profiles associated with a conventional dichroic filter and a conventional emission filter. As shown, it is quite possible that there may be some overlap between the spectrum of the excitation light and the spectrum of the emission from the specimen, creating unwanted noise in the response received at the detector. While on the scale of FIG. 5 the overlap (appearing between about 0-10% transmission region) appears to be relatively slight, when viewed on the log scale it becomes evident and can lead to errors in the measured output. The response of a tunable emission filter may be deconvolved in software to reduce the effects of the overlap and provide more accurate results (for an increase in cost and, perhaps, a delay in response). Alternatively, this problem has been addressed in the prior art through the utilization of an excitation filter with very tight requirements (an additional expense).

Figure 6:
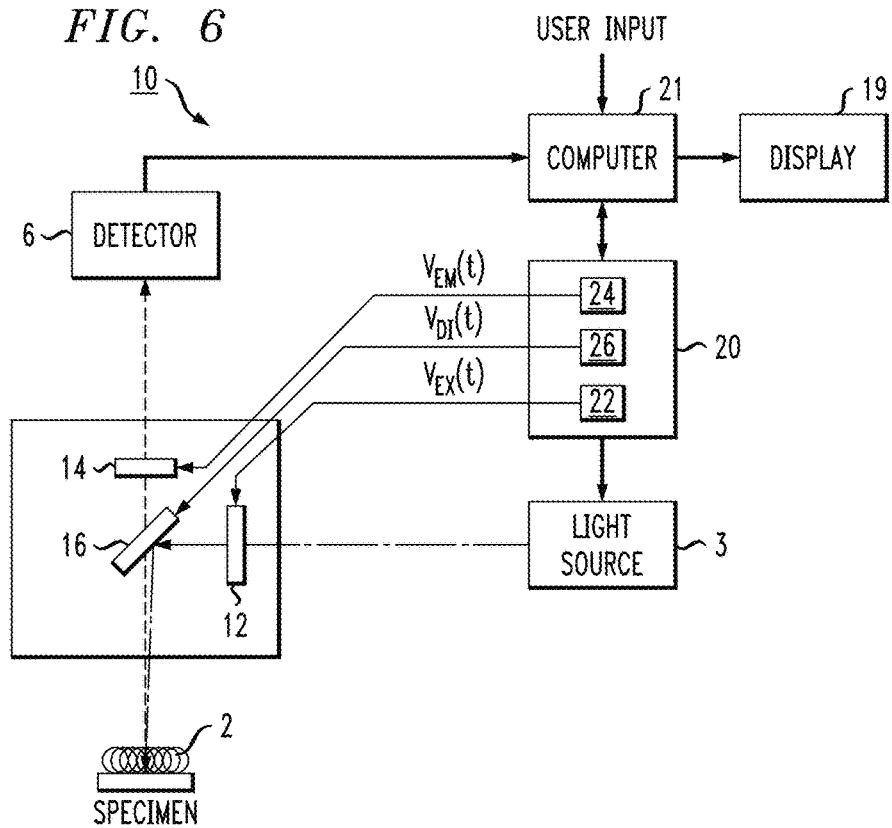
FIG. 6 illustrates an exemplary fluorescence spectrometer formed in accordance with an embodiment of the present invention.

These various wavelength-dependent filter response problems are addressed by the present invention; specifically, by the utilization of voltage-tunable filters for one or more of the excitation, emission, and dichroic filters in a fluorescence-based imaging system. FIG. 6 illustrates an exemplary fluorescence microscope 10 formed in accordance with one embodiment of the present invention. As shown, light source 3, specimen 2 and detector 6 of microscope 10 may be similar to the like-numbered elements shown in prior art FIG. 1. However, in contrast to the prior art arrangements, microscope 10 of the present invention further comprises one or more voltage-tunable filters, shown as a voltage-tunable excitation filter 12, a voltage-tunable emission filter 14 and a voltage-tunable dichroic filter 16.

Also shown in FIG. 6 is a system voltage controller 20 that is utilized to provide tunable voltage inputs (including a set of voltages) to each of the filters (under the control of the user) to create the desired filter responses for a given application. A first tunable voltage source 22 is utilized to provide a tunable voltage $V_{EX}(t)$ to excitation filter 12, a second tunable voltage source 24 is utilized to provide a tunable voltage $V_{EM}(t)$ to emission filter 14, and a third tunable voltage source 26 is utilized to provide a tunable voltage $V_{Df}(t)$ to dichroic filter 16. In accordance with the present invention and discussed in detail below, each voltage source is individually controlled (in response to instructions from an associated computer system 21) in a manner that allows for the characteristics of each filter to be individually tailored (and, within each filter, the ability to independently adjust the CWL and BW of the filter). For example, computer system 21 may respond to user input (and/or feedback from detector 6) to determine if any adjustment in any of the applied voltages is required. Also shown in FIG. 6 is a display device 19 that may be used to provide a visual indication of the results generated by the combination of controller 20 and computer system 21.

In accordance with one embodiment the present invention, each tunable filter includes a series combination of a shortwave pass (SWP) filter and a longwave pass (LWP) filter, with separate control voltages applied to each to separately modify the passband of each filter. Alternatively, it is possible to maintain one filter of the pair as a "fixed" filter, and adjust the parameters of the remaining filter. While not providing the same range of variation for CWL and BW, there are certainly situations where the convenience of maintaining one filter as a "fixed" filter and needing to adjust only one of the remaining filters provides a sufficient degree of flexibility for the intended use of the filter.

Figure 7:
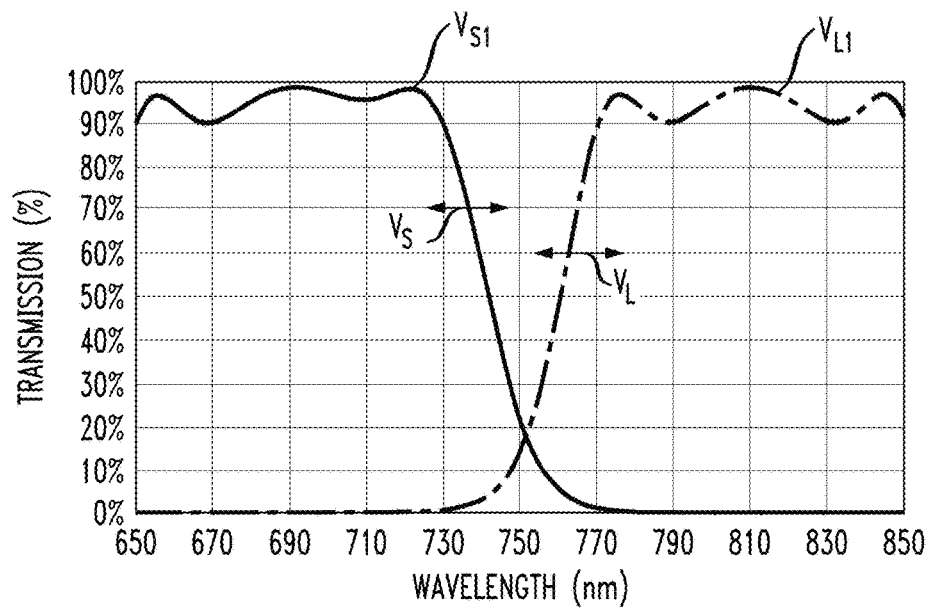
FIG. 7 illustrates exemplary spectral responses for a shortwave pass (SWP) filter and a longwave pass (LWP) filter.

FIG. 7 illustrates exemplary responses for a SWP filter with an applied voltage $V_{S1}$ and a LWP filter with an applied voltage $V_{L1}$. In this case, there is very little overlap in passbands for these two filters. However, in accordance with the principles of the present invention, it is possible to increase ("tune") the amount of overlap (defining the bandwidth of the combined filter) as well as adjust ("tune") the center wavelength (CWL) of the overlap by modifying the voltage applied to each filter.

Figure 8:
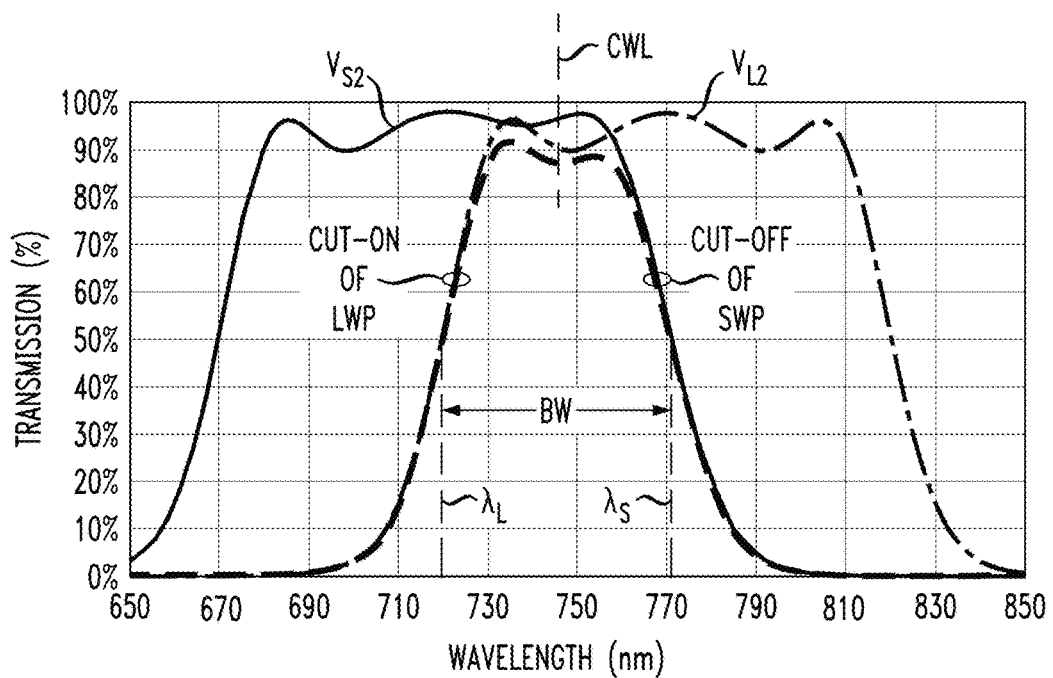
FIG. 8 illustrates the utilization of a series combination of voltage-controlled SWP and LWP filters in accordance with the present invention.
Figure 9:
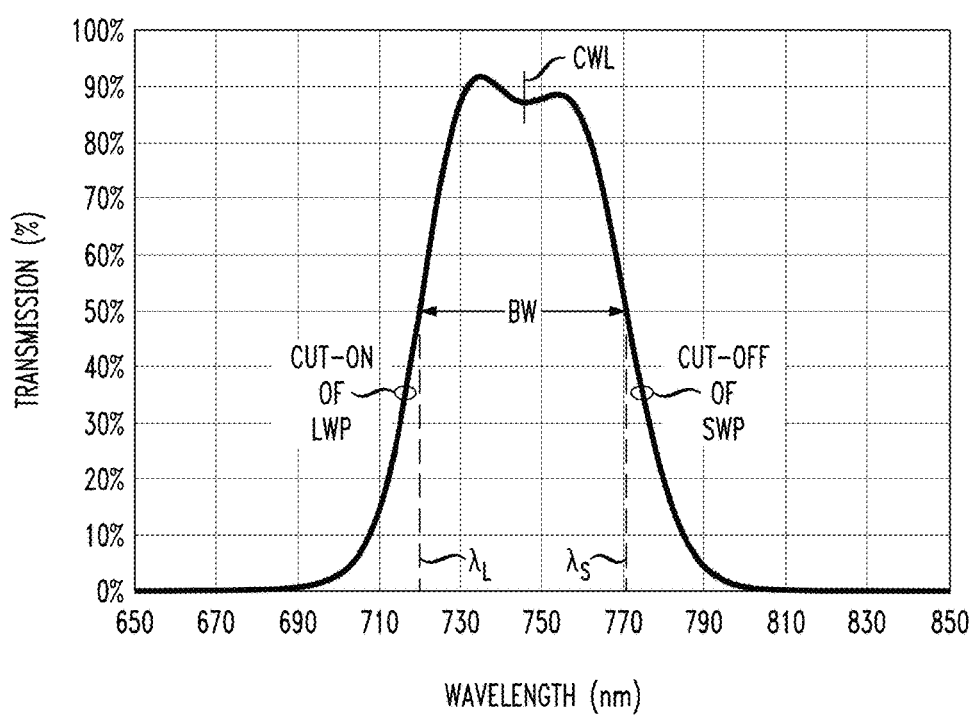
FIG. 9 shows in particular the overlap in spectral responses for the pair of SWP and LWP filters as shown in FIG. 8.

FIG. 8 illustrates the utilization of a series combination of voltage-controlled SWP and LWP filters in accordance with the present invention to provide a tunable filter response, particularly useful in the imaging applications described above. In comparing the plots of FIG. 8 to those of FIG. 7, it is shown that the application of a different voltage (or set of voltages) is applied to the SWP filter, the bandwidth of the SWP filter is extended. Similarly, the application of a different voltage (or set of voltages) to the LWP extends its bandwidth as well. The series combination of these devices thus results in a filter response of the overlapped regions of the two filters, defined as the bandwidth between the "cut-on" wavelength $\lambda_L$ of the LWP filter and the "cut-off" wavelength $\lambda_S$ of the SWP filter. The overlapped area is shown clearly in FIG. 9, where the CWL and BW of this filter response is also shown.

Figure 10:
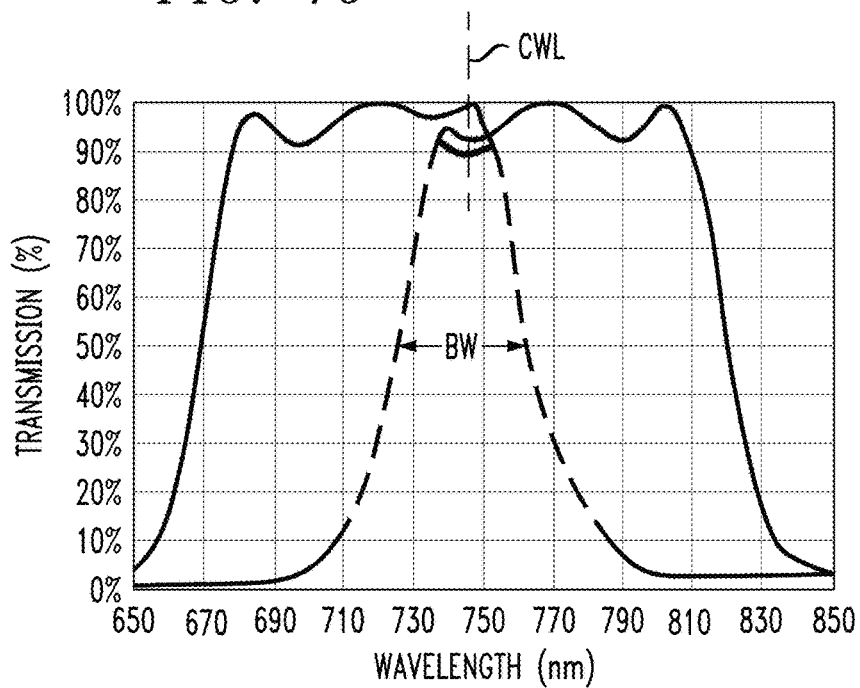
FIG. 10 shows an alternative response for the combination of the SWP and LWP filters (controlled by changes in applied voltages), providing a change in the bandwidth of the overall filter.
Figure 11:
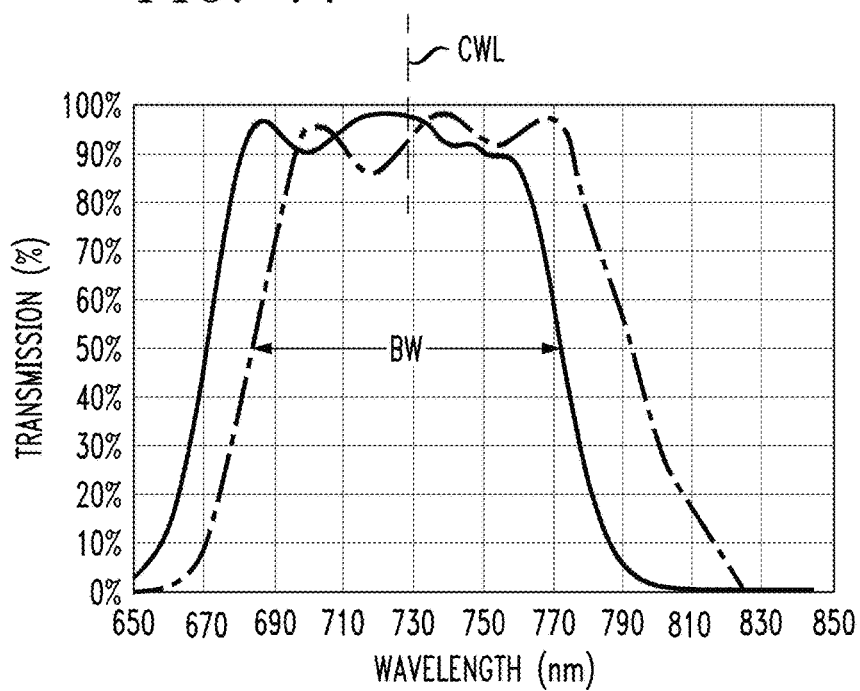
FIG. 11 shows another alternative response for the combination of the SWP and LWP filters (again, controlled by changes in applied voltages), in this case providing a change in the bandwidth of the overall filter.
Figure 12:
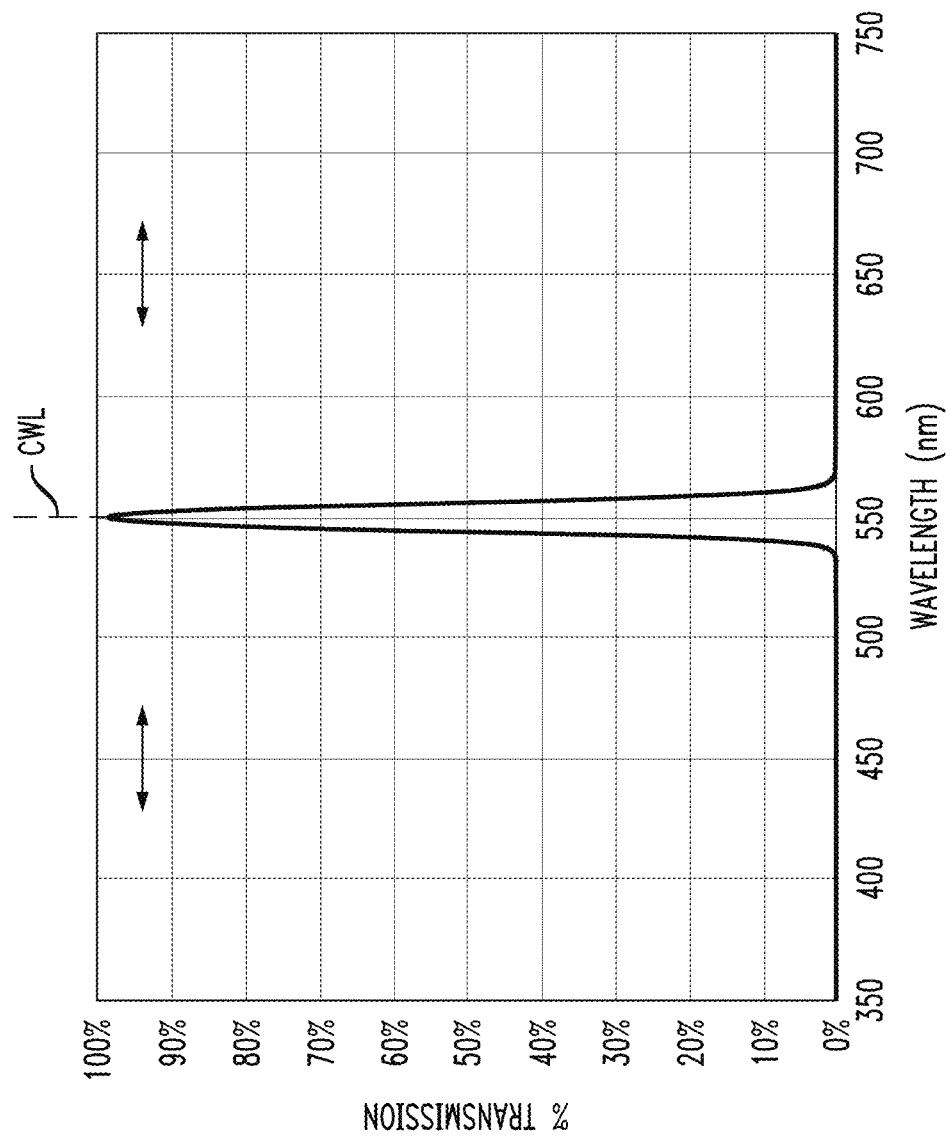
FIG. 12 is a graph of a relatively narrowband filter that may be created by modifying the voltages applied to the SWP and LWP filters in the configuration of the present invention.

As mentioned above, by virtue of adjusting the voltage applied to each of these filters (or only one filter, if desired), it is possible to adjust (independently) the BW and CWL of the combined response. FIG. 10 illustrates one variation to the plots of FIG. 8, in this case modifying the response of the SWP and LWP filters to change the BW of the combined response. FIG. 11 illustrates another variation, where in this case the applied voltages are adjusted to change the BW of the combined response. Indeed, it is possible to control the voltages applied to the SWP and LWP filters in a manner that creates an extremely narrowband response, as shown in FIG. 12. With the ability to create this type of narrowband response, it is further possible in accordance with the present invention to tune the CWL of this narrowband response by adjusting the filter responses of the SWP and LWP filters in a synchronous manner, thus creating a "sweeping" type of adjustable filter, particularly useful when needing to monitor results at the output of the emission filter in the configuration as shown in FIG. 6. The ability to sweep across a narrowband response in this manner is considered to be particularly useful in high-speed applications, such as measuring the reactions of bio-medical specimens in real time.

Figure 13:
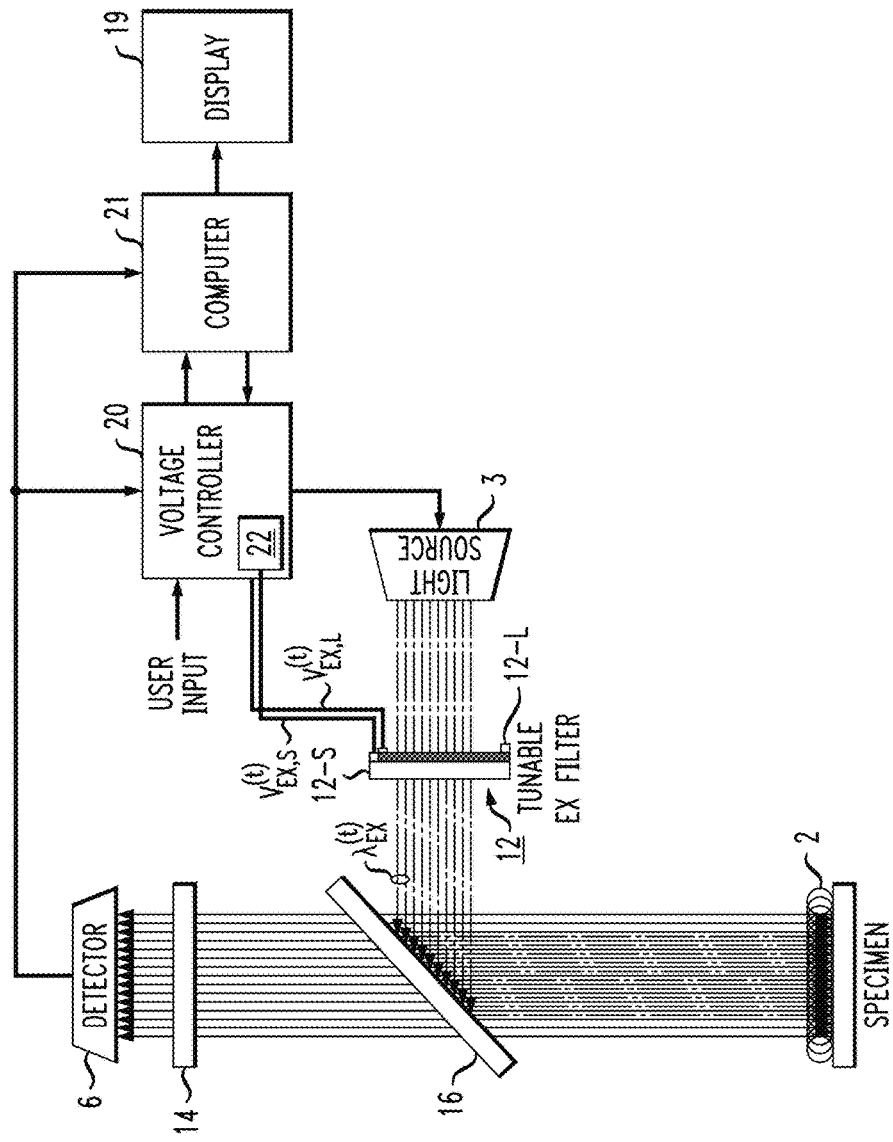
FIG. 13 illustrates a specific embodiment of the present invention, in this case utilizing a voltage-controlled tunable optical filter as the excitation filter in a fluorescence spectrometer.

FIG. 13 illustrates a specific embodiment of the present invention where a series combination of a voltage-controlled SWP filter 12-S and a voltage-controlled LWP filter 12-L is used in the formation of tunable excitation filter 12. As shown, a pair of tunable voltages (or sets of voltages) $V_{EX,S}$ and $V_{EX,L}$ are applied to filters 12-S and 12-L, respectively. With the ability to tune the response of excitation filter 12, it is possible to continuously adjust the wavelength of the input illumination reaching specimen 2, denoted $\lambda_{EX}(t)$. In this particular embodiment, both emission filter 14 and dichroic filter 16 remain "fixed" in their spectral response.

As also shown in FIG. 13, voltage controller 20 includes a tunable voltage source 22 that is used to modify the voltages (or sets of voltages) $V_{EX,S}$ and $V_{EX,L}$ applied to filters 12-S and 12-L. In the manner described above with FIGS. 7-12, changes in voltages for the SWP and LWP filters allow for the BW and CWL of tunable excitation filter 12 to be varied as desired. With this capability, a variety of different non-overlapping dyes (with difference excitation wavelengths) may be used with specimen 2, without requiring any replacement of the excitation filter, as was necessary in the prior art.

While the inventive voltage-controlled tunable excitation filter 12 as shown in FIG. 13 is able to perform measurements on specimen 2 at various different wavelengths, the ability to control the BW and CWL in the manner discussed above also provides for the ability to modify the actual process of providing different wavelengths to specimen 2. Additionally, it is possible to control the "on" and "off" of the excitation wavelength, creating a type of "shutter" for use in analyzing specimen 2. That is, if the bandwidths of the SWP and LWP filters are shifted (by applied voltages) such that there is no overlap in their spectra, there will be no optical signal illuminating specimen 2 (creating the "off" condition). Various other possible combinations of spectral response of the SWP and LWP filters may be envisioned by those skilled in the art to create other types of excitation light sources for fluorescence applications.

Figure 14:
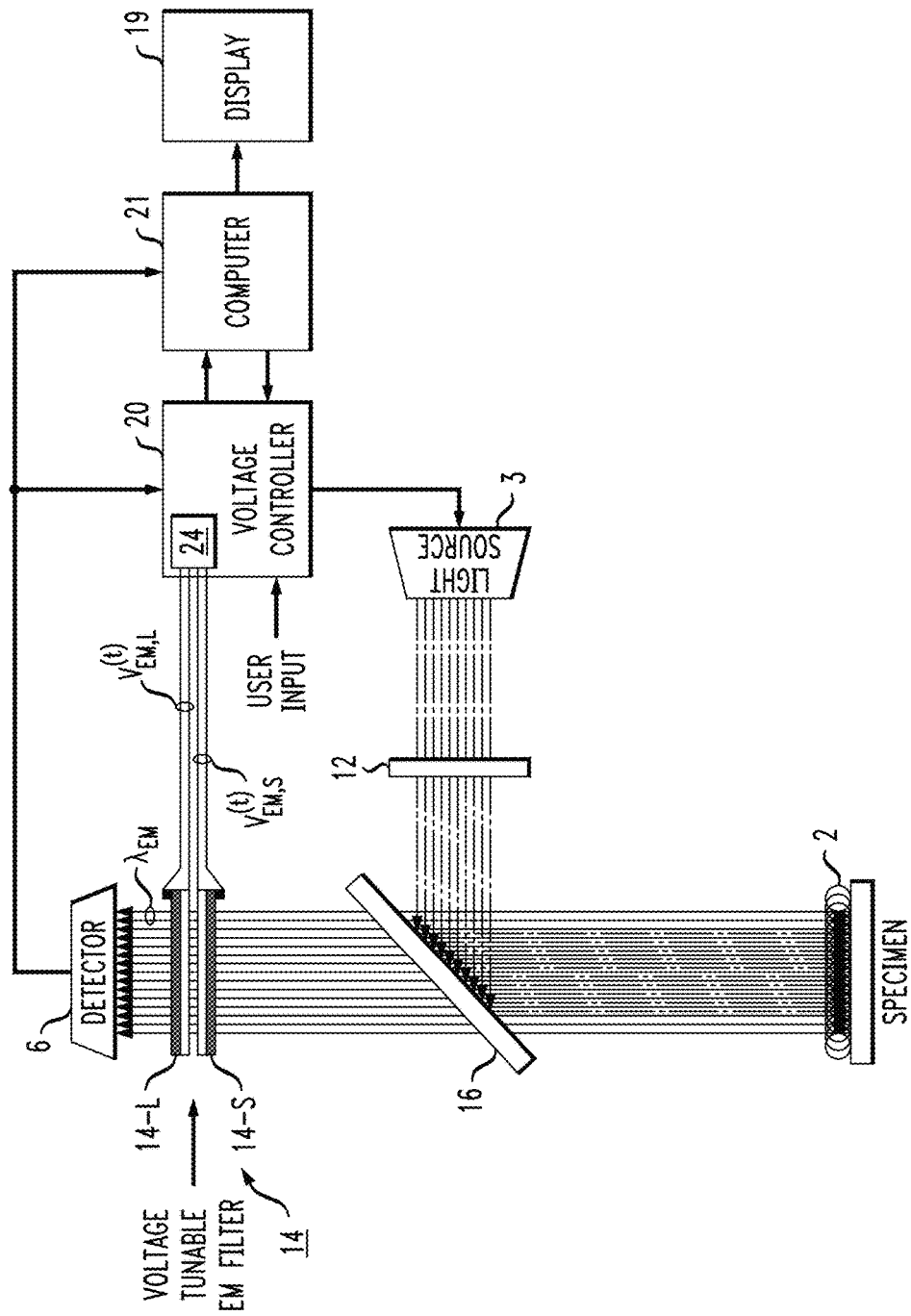
FIG. 14 illustrates another embodiment of the present invention, in this case utilizing a voltage-controlled tunable optical filter as the emission filter in a fluorescence spectrometer.

FIG. 14 shows another embodiment of the present invention, in this case where a voltage-controlled tunable emission filter 14 is utilized. This is shown in FIG. 14 as 14-S (for the SWP filter) and 14-L (for the LWP filter). Voltage control signals $V_{EM,S}$ and $V_{EM,L}$ from voltage source 24 in voltage controller 20 are used to adjust the spectral responses of these filters to create the desired BW and CWL for the emission filter. For example, as shown in FIG. 12, an extremely narrowband response may be swept across a relatively broad wavelength range, searching for the particular wavelength range with the strongest response. Various computer-based systems are available for performing this type of coordinated wavelength sweeping and response measuring type of functionality. That is, by being able to adjust the CWL and BW, the user is able to "tune" the emission filter so as to lock onto the strongest signal (i.e., the particular wavelength(s) associated with the maximum output).

Figure 15:
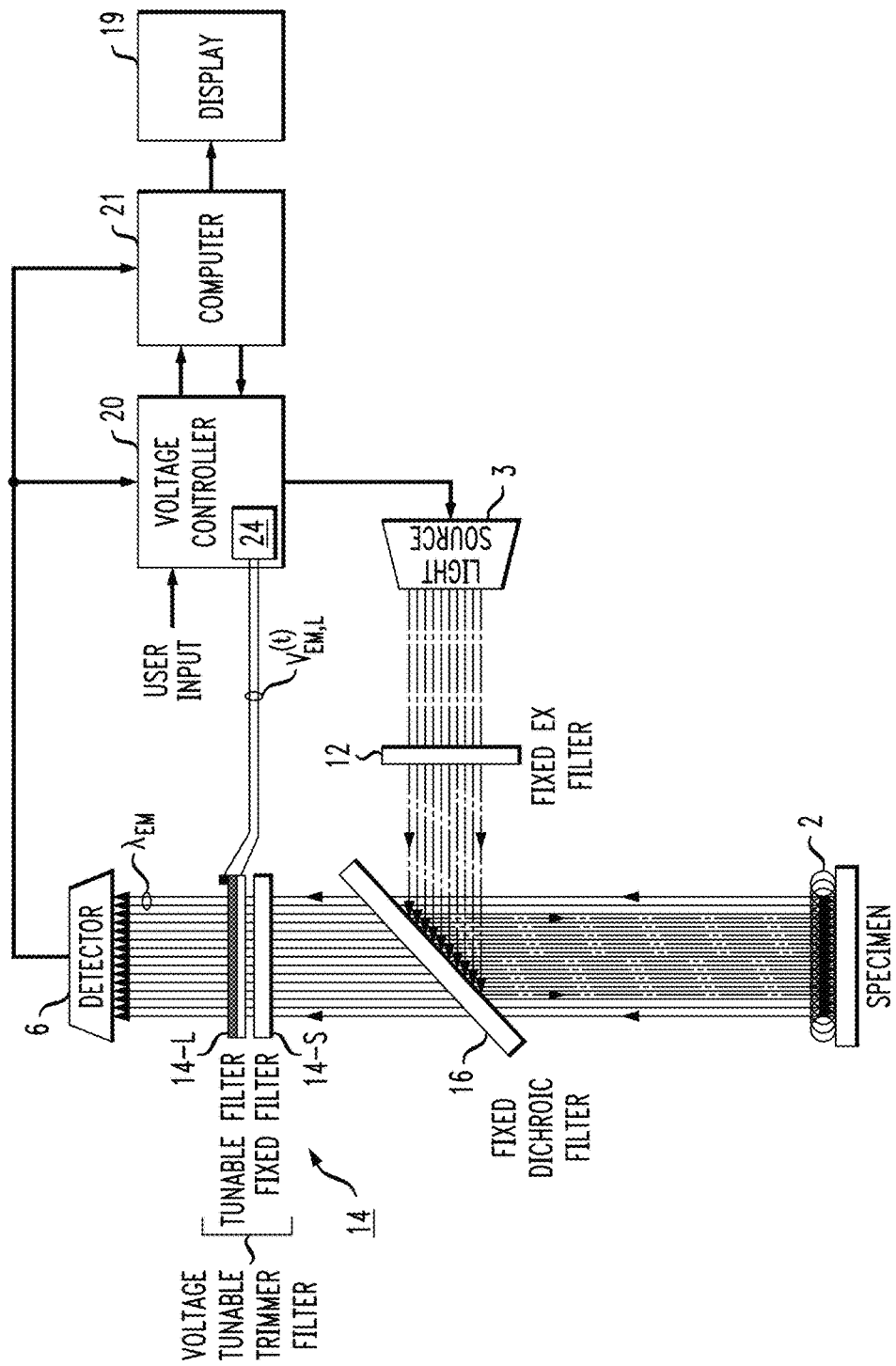
FIG. 15 shows an alternative configuration of the embodiment of FIG. 14, in this case using a "fixed" emission filter in combination with a tunable emission filter, the tunable emission filter utilized to fine-tune ("trim") the spectral response of the emission filter.

In some cases, it is possible that the tuning required for emission filter 14 does not need to cover an extensive range (as may be used for excitation filter 12). FIG. 15 illustrates an alternative configuration of the embodiment of FIG. 14, in this case using a combination of a "fixed" filter and "tunable" filter in the formation of emission filter 14. As mentioned above, one embodiment of the present invention contemplates holding one filter fixed (for example, the SWP filter) and only adjusting the spectral response of the remaining filter (here, the LWP filter). The adjustment of only one of the filters provides the same type of adjustments in CWL and BW, but over a smaller range. In this case, the function of tuning can be thought of as "trimming" the response of the filter to hone in on the proper wavelength.

Figure 16:
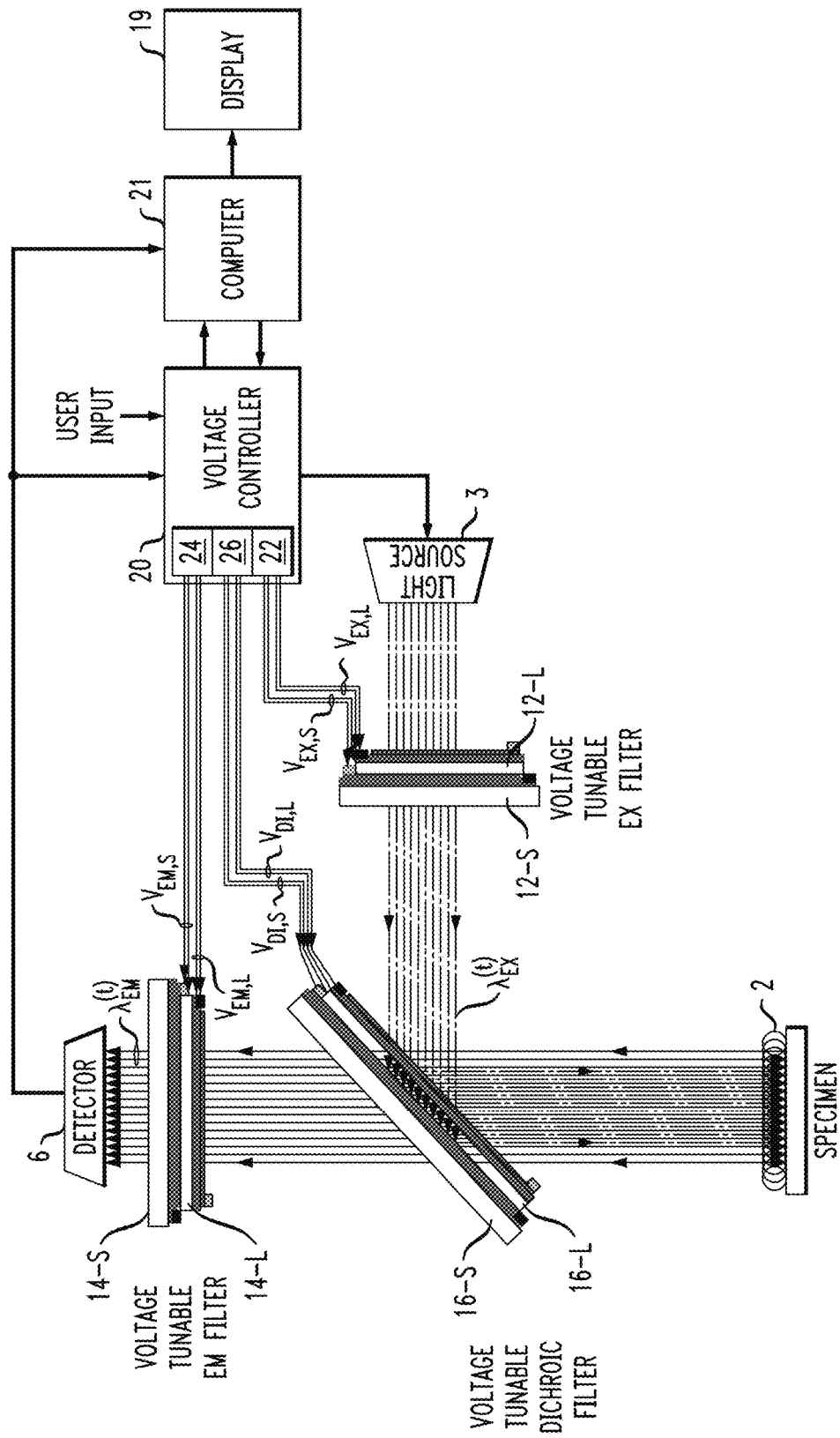
FIG. 16 illustrates yet another embodiment of the present invention, in this case comprising a fluorescence spectrometer that utilizes voltage-controlled tunable optical filters for the excitation filter, dichroic filter and emission filter.

FIG. 16 illustrates an alternative fluorescence spectrometer formed in accordance with the present invention, where in this case all three filters 12, 14 and 16 are formed as voltage-controlled tunable filters in accordance with the present invention. In this configuration, voltage controller 20 is shown as including three separate tunable voltage sources 22, 24 and 26. As with the embodiment shown in FIG. 13, tunable voltage source 22 is used to provide adjustable voltages $V_{EX,S}$ and $V_{EX,L}$ to excitation filters 12-S and 12-L to allow for adjustment in the excitation wavelength directed onto specimen 2 (different wavelengths activating different dyes). As with the embodiment shown in FIG. 14, tunable voltage source 24 utilized to provide adjustable voltages $V_{EM,S}$ and $V_{EM,L}$ to SWP emission filter 14-S and LWP emission filter 14-L, respectively.

Given the tunability of excitation filter 12 and emission filter 14, it is advantageous to also be able to change the response to dichroic filter 16. Thus, voltage controller 20 is shown in FIG. 16 as further comprising a tunable voltage source 26 that is used to adjust the response of the pair of filters 16-S and 16-L used to form tunable dichroic filter 16.

Figure 17:
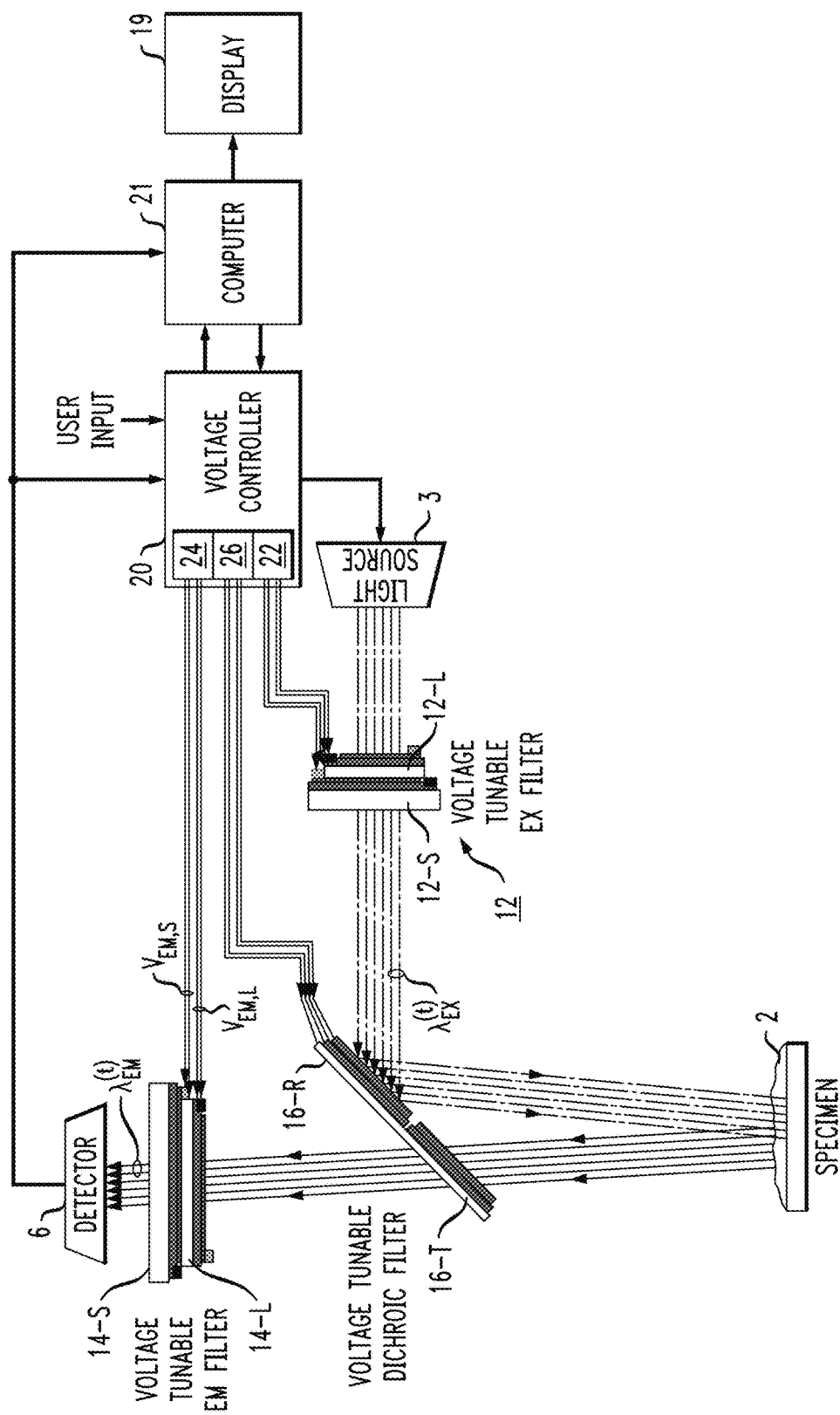
FIG. 17 illustrates another configuration of the embodiment of FIG. 14, in this case using a pair of separate filter components in the implementation of the tunable dichroic filter.

FIG. 17 illustrates an alternative configuration for the embodiment shown in FIG. 16. In this case, a pair of filters is used to form dichroic filter 16. In particular, a specific type of filter that may be utilized in the systems of the present invention (and discussed in detail below) functions to transmit a specific wavelength band and "absorb" the remaining wavelengths. Thus, in order to provide the necessary wavelength re-direction actions between light source 3, specimen 2 and detector 6, dichroic filter 16 is shown as comprising a reflecting, voltage-controlled tunable filter 16-R and a transmitting, voltage-controlled tunable filter 16-T. Tunable filter 16-R is shown as receiving the excitation wavelength signal from excitation filter 12, and re-directing this wavelength toward specimen 2 (all other wavelengths absorbed by tunable filter 16-R). Tunable filter 16-T is shown as receiving the optical signal emitted by specimen 2, and allowing the emission wavelength to pass through filter 16-T and be directed toward emission filter 14. All other wavelengths outside of the emission band are absorbed by filter 16-T.

With this understanding of various fluorescence microscopy applications where a voltage-controlled tunable optical filter may be used, the following portion of the specification (associated with FIGS. 18-27) describes exemplary types of devices that may be utilized as the actual voltage-controlled tunable optical filter devices.

Figure 18:
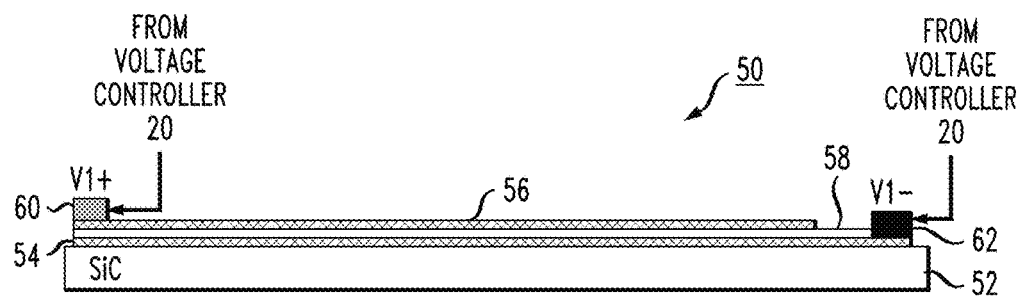
FIG. 18 is a diagram of an exemplary voltage-tunable plasmonic optical filter useful in the formation of the SWP or LWP filters in accordance with the present invention.

FIG. 18 is a side view of an exemplary voltage-tunable optical filter 50 particularly configured for use as either the SWP filter or LWP filter (based on the applied voltages, as well as the width and spacing of the strips used to form the device) in the inventive imaging system applications. In this particular embodiment, optical filter 50 is a plasmon-based device formed on a substrate 52 that is transmissive over the wavelength range of interest. A graphene layer 54 is disposed over a top major surface of substrate 52. A plurality of graphene strips 56 is shown as overlying graphene layer 54, with a layer of an insulating material 58 disposed between graphene layer 54 and graphene strips 56. A pair of electrical contacts 60, 62 is used to provide the tunable voltage to the structure. It is to be understood that the utilization of graphene in the formation of a plasmonic filter is exemplary only, various other transparent conductive materials may be used (for example, indium tin oxide (ITO)) as the voltage-controlled element in the plasmonic device.

The various prior art "tunable" optical filters were only able to provide adjustments at kHz speeds (at best). Advantageously, a plasmonic graphene-based optical filter formed in accordance with the present invention is able to be tuned at speeds of tens of GHz, or more (limited only by the RC time constant of the capacitance between the strips and the conductive plane and the resistance in the leads). The material used to form substrate 52 is limited mainly by the wavelength range of the desired transmission. $SiO_2$ is an acceptable choice as a substrate material for wavelengths in the UV to near-IR range; sapphire ($Al_2O_3$) is useful for the 150 nm-5500 nm range. SiC is another material that is transmissive over acceptable wavelength ranges. Mono- or polycrystalline CVD diamond is also an excellent material choice, since it has the widest transparency region of any material and a straightforward graphitization process can be used to create the necessary graphene layer over its surface. Of course, the expense of this material may limit its usefulness to "mission critical" applications. In some cases, a flexible polymer (such as polymethyl methacrylate, PMMA) may be used as the substrate, allowing for three-dimensional curvature of the filter to be an option.

Figure 19:
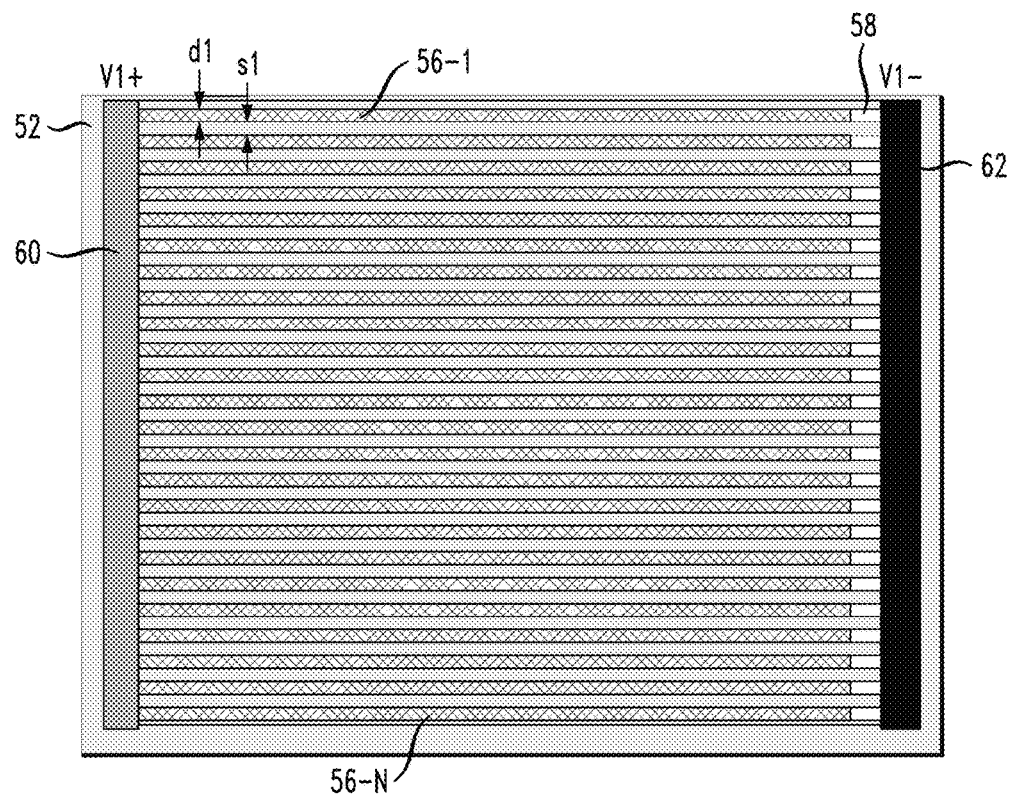
FIG. 19 is a top view of the filter shown in FIG. 18.
Figure 20:
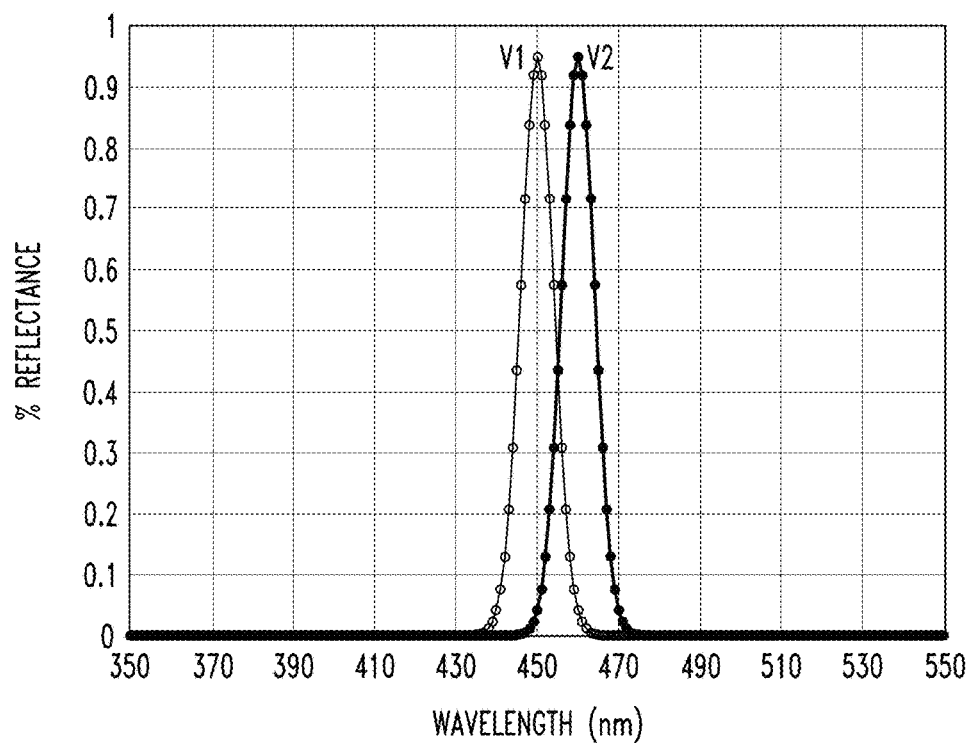
FIG. 20 is an exemplary spectral response of the plasmonic optical filter as shown in FIG. 18.

FIG. 19 is a top view of optical filter 50, illustrating the particular configuration of a plurality of N graphene strips 56, as visible from above filter 50. The width of an individual strip 56-1 is shown as d1 in FIG. 19, with the separation between adjacent strips defined as s1 in FIG. 19. Electrical contacts 60 and 62 are shown as metal conductors extending across the surface of filter 50 in a direction perpendicular to strips 56. FIG. 20 illustrates the spectral response of filter 50, in particular when a given voltage $V_1$ is applied to electrical contact 60 and a given voltage $V_2$ is applied to electrical contact 62. The response is plotted as a percentage of reflection (or absorbance) as a function of wavelength. In the case of graphene-based plasmonic filters, the reflection is a function of the conductivity of the graphene. High conductivity graphene gives a reflective resonance; low conductivity graphene gives an absorptive resonance.

Figure 21:
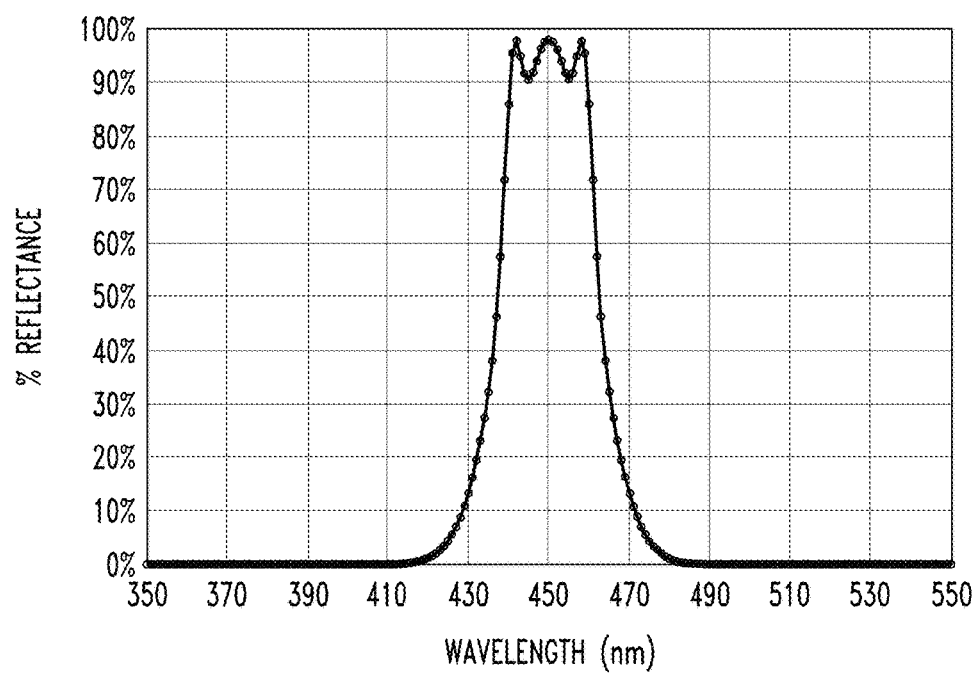
FIG. 21 shows the spectral response of an exemplary plasmonic filter obtained by changing the geometry of the filter (e.g., changing the width and/or spacing of the strips)

FIG. 21 illustrates a multiple resonance spectral response that may be created by a modification of the voltages applied to contacts 60 and 62 or, alternatively, by changing the geometry of filter 50. For example, changing the width of strips 54 (and/or the spacing between adjacent strips) may provide a multiple resonance response.

FIG. 22 illustrates an exemplary voltage-controlled optical filter 70 formed in accordance with the present invention for use as, for example, an excitation filter or emission filter in a fluorescence microscopy application. Filter 70 utilizes a pair of devices of a form similar to that shown in FIGS. 18 and 19, where one filter is disposed on top of the other filter (i.e., the pair of filters are built upon a common substrate). In the exemplary illustration of FIG. 22, a LWP filter 72 is shown as formed on a substrate 74, with a SWP filter 76 disposed over LWP filter 72. Each filter is formed to include spaced-apart layers of graphene (the top layer being in the form of strips), with an additional dielectric layer 78 formed between the two filters 72, 76. The spectral response for this configuration, depicted as transmission percentage, is shown in FIG. 23, where graph (a) in FIG. 23 is associated with a configuration where the voltages applied to filters 72 and 76 are closely-spaced, resulting in a significant overlap between the responses of the filters (creating a wideband output filter response). The profile in graph (b) is associated with an alternative configuration where the voltages applied to the two filters yields little overlap between their spectral responses (creating a narrowband output filter response). Other values of $V_1$ and $V_2$ will thus create profiles between these two extremes.

Figure 24:
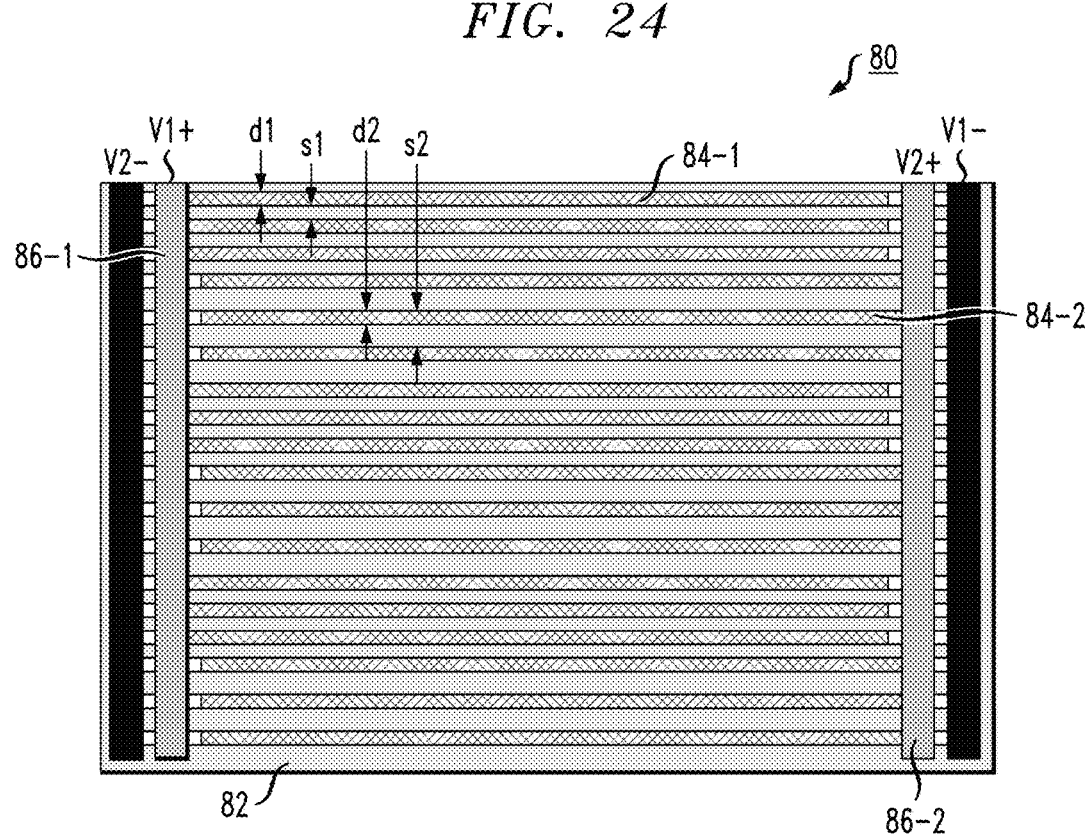
FIG. 24 shows a different filter geometry that has been found to yield a wider bandwidth.

FIG. 24 is a top view of an alternative filter configuration 80 that is able to achieve a wider bandwidth by creating second- and third-order resonances in the filter structure by incorporating different widths d and/or separations s in the filter structure. In another configuration, it is possible to apply separate voltages to separate regions of the filter structure itself. As with the embodiments described above, filter 80 is built upon a common substrate 82 (that is, the LWP and SWP filters are positioned one on top of the other). A first plurality of graphene strips 84-1 is shown as having a diameter d1, with a separation of s1 between adjacent strips. A second plurality of graphene strips 84-2 is shown as having a diameter d2, with a spacing of s2 between adjacent strips.

For the particular embodiment shown in FIG. 24, a first set of three relatively thin graphene strips 84-1 is positioned from a front edge inward along the top surface of filter 80. A set of three relatively thick graphene strips 84-2 is then positioned next to the set of relatively thin strips 84-1. This pattern of alternating sets of three strips extends across the surface of filter 80 as shown. In operation, a first electrical contact 86-1 is used to apply a (tunable) voltage V1 to the plurality of relatively thin graphene strips 84-1. A second electrical contact 86-2 is used to apply a tunable voltage V2 to the plurality of relatively thick graphene strips 84-2 (similar connections for the remaining voltage connections are shown in FIG. 24).

Figure 25:
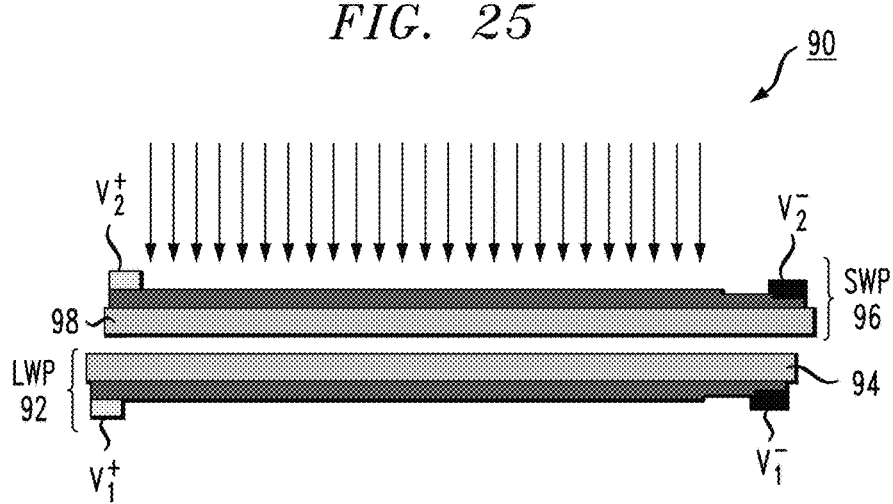
FIG. 25 illustrates an alternative embodiment of a voltage-controlled optical filter, in this case with the SWP and LWP filter components formed on separate substrates.

FIG. 25 illustrates an alternative embodiment of a voltage-controlled filter 90 in accordance with the present invention. In this case, each filter is formed on its own substrate, simplifying the fabrication process while necessitating an increase in the overall size of the filter. Simply, filter 90 includes a LWP filter 92 formed on a first substrate 94 and a SWP filter 96 formed on a second substrate 98. Each filter is formed of a set of graphene strips disposed over a planar layer of graphene (with an insulating layer separating the planar layer from the strips). As with the configurations described above, each filter is controlled by separate applied voltages.

Figure 26:
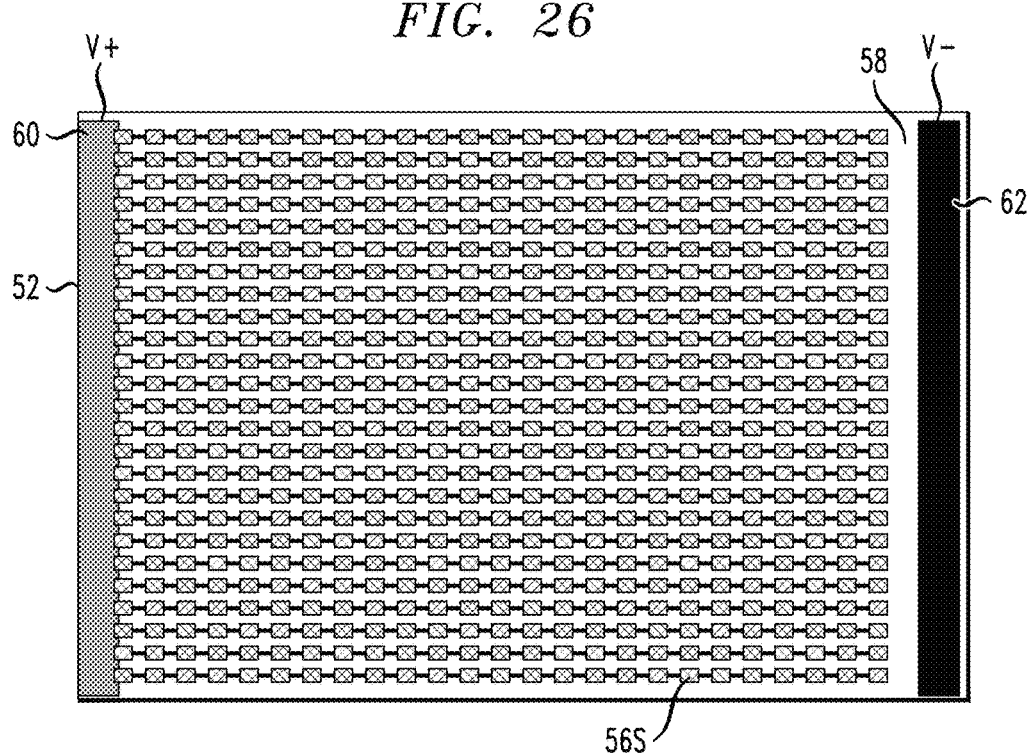
FIG. 26 is a top view of a polarization-insensitive embodiment of the optical filter as shown in FIG. 19.
Figure 27:
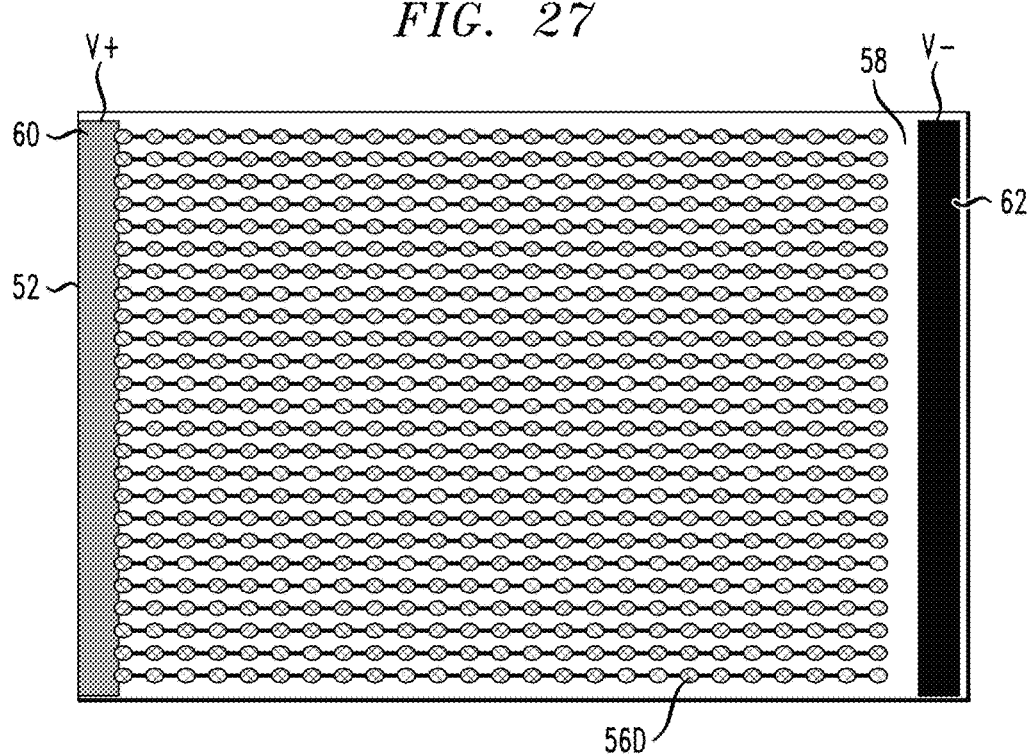
FIG. 27 is a top view of an alternative polarization-insensitive embodiment, in this case using a plurality of graphene "dots" in the formation of the filter.

In certain cases, it may be required to control (or maintain) the polarization of the optical signal used as the excitation source (for example). In these situations, a polarization-insensitive voltage-controlled tunable filter would be preferred. FIG. 26 is a top view of one exemplary polarization-insensitive variation of the plasmon-based device as shown in FIG. 19. Here, the plurality of graphene strips 56 is replaced by a two-dimensional arrangement of graphene squares 56S (which may be formed by using a different lithographic pattern in the fabrication process for this graphene layer). An alternative polarization-insensitive configuration is shown in FIG. 27, which utilizes a two-dimensional arrangement of graphene dots 56D (formed using a different lithographic pattern), in the form of quantum dot chains.

As mentioned above, there are imaging systems used in other types of instrumentation that may also benefit from the utilization of voltage-controlled filters formed in accordance with the present invention. For example, Raman spectroscopy is a analysis tool that differs from fluorescence microscopy as described above in that Raman-based analysis detects vibrational and rotational resonances of a specimen (particularly, of the molecules forming the specimen) created in response to being illuminated with a high power optical signal. Raman spectroscopy thus works directly with the specimen being studied and does not require any type of fluorescence dye or marker.

Inasmuch as a Raman spectrometer is measuring changes in the vibration or rotation of molecules, it is typical that the Raman signal emitted from a specimen is orders of magnitude smaller than the fluorescence emission signals discussed above. As a result, it is typically required to utilize high power laser sources to illuminate the specimen (capable of generating a very narrowband signal). The excitation filter should therefore be tuned, in accordance with the present invention, to create this narrowband signal and reduce the possibility of any extraneous amplified stimulated emission (ASE) noise. The emission filter is preferably configured (via voltage control) to be a very deep notch filter (i.e., high optical density) that is tuned to the wavelength of the excitation laser source.

Figure 28:
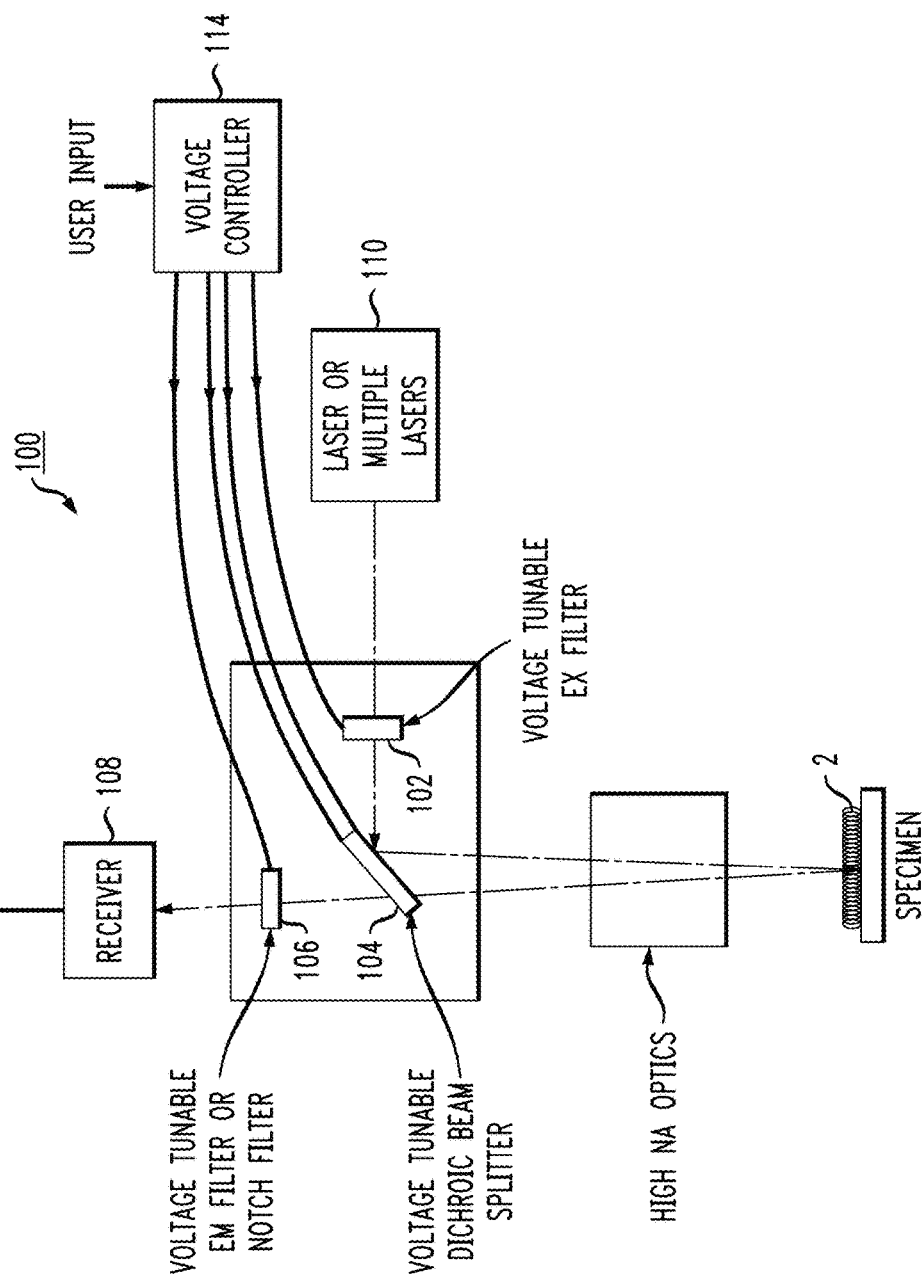
FIG. 28 illustrates an exemplary Raman spectrometer configured to include voltage-controlled tunable optical filters in accordance with the present invention.

FIG. 28 is a diagram of a typical Raman spectrometer, which is similar in form to the various fluorescence spectrometers described above in the fact that it may utilize a "filter cube" 100 to maintain the integrity and directionality of the various optical signals. As shown, Raman filter cube 100 comprises a voltage-tunable excitation filter 102, a voltage-tunable dichroic beam-splitter 104 and a voltage-tunable emission filter 106. In association with the low power of the optical signals arriving at a receiver 108, emission filter 106 is very likely a notch filter, tuned to the excitation wavelength.

Figure 29:
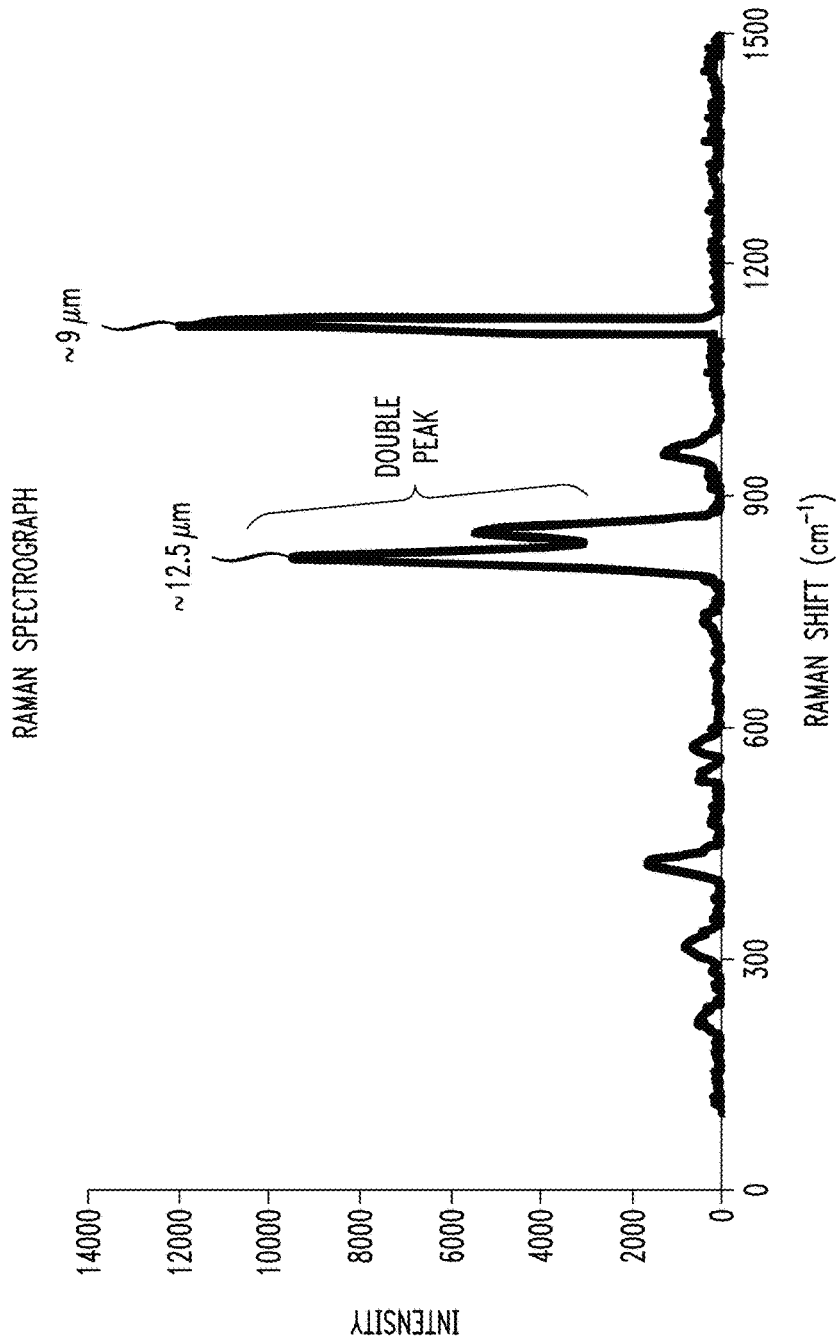
FIG. 29 is a plot of response from a Raman spectrometer (i.e., spectrograph)

FIG. 29 is an exemplary Raman spectrograph, depicting a typical signal as presented to receiver 108. Here, there is a double peak at about 12.5 µm (800 cm$^{-1}$), with another peak at about 9 µm (1100 cm$^{-1}$), corresponding to the interaction of the light with the vibrational energy levels in the specimen being studied. As shown, various ones of the peaks may be very narrow and difficult to detect with prior art types of systems. Similarly, features such as a "double-peak" or low-level peaks may also be difficult to discern.

Accordingly, in order to obtain any useful level of information at detector 108, a high-power laser source 110 is required, operating at a specific wavelength that will create the vibrational reaction in the specimen. Here, excitation filter 102 is controlled by changing applied voltages, in accordance with the present invention, to narrow the "line" of laser source 110 and ensure that amplified spontaneous emission (ASE) noise is substantially reduced.

Figure 30:
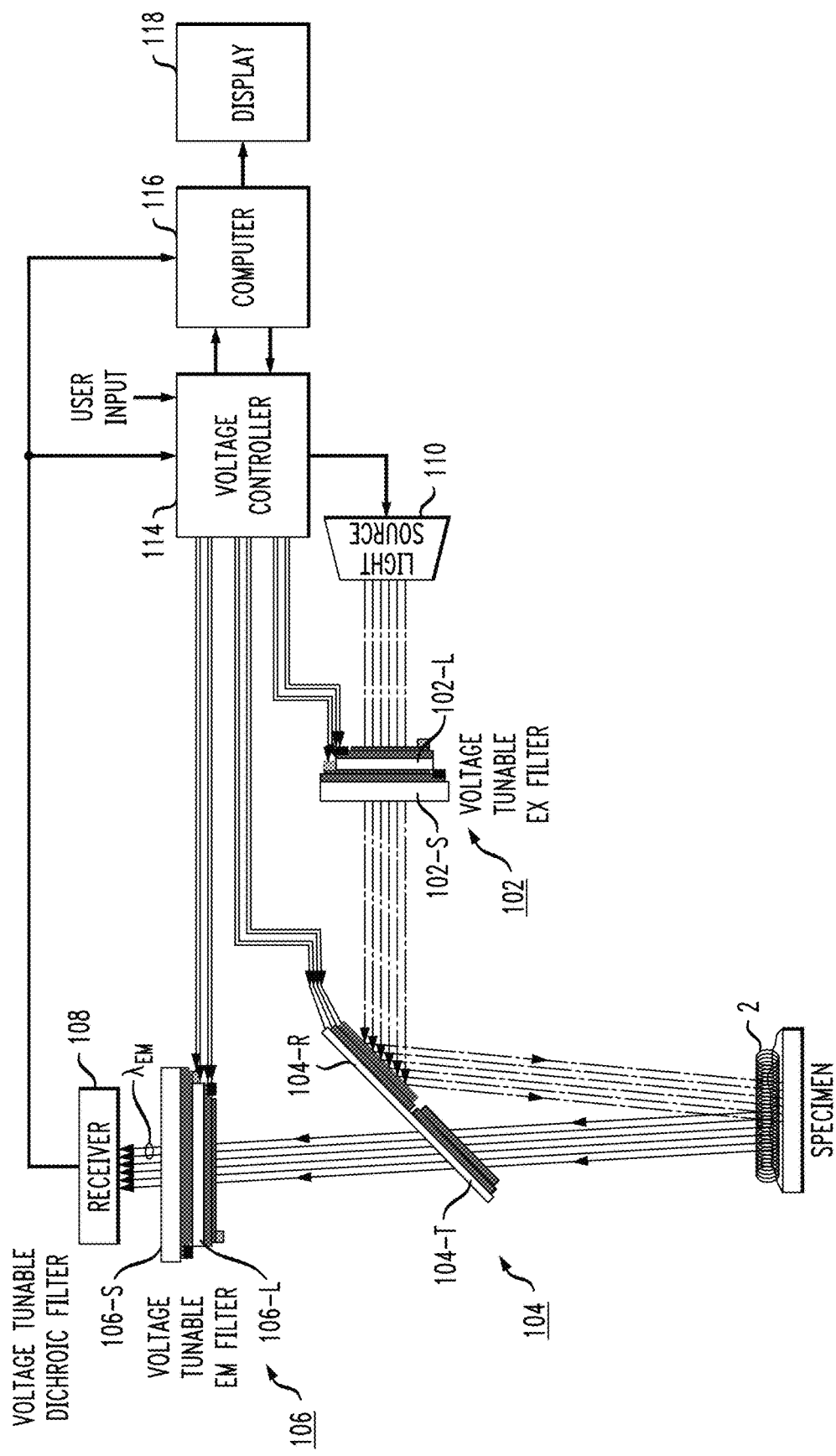
FIG. 30 illustrates an exemplary multisource Raman spectrometer.

Beyond providing the capability to tune the filter block to match the wavelength of laser source 110, the utilization of voltage-controlled filters in accordance with the present invention allows for the same filter cube 100 to be utilized in Raman spectroscopy systems that include multiple laser sources operating at different wavelengths, for the reasons discussed above. FIG. 30 illustrates an exemplary multi-source Raman spectrometer based upon the simplified diagram shown in FIG. 28. Here, the structure of exemplary tunable filter configurations are illustrated for excitation filter 102, dichroic filter 104, and emission filter 106. Additionally, light source 110 is considered to include a plurality of separate high power laser sources, each emitting a different wavelength used to probe a different molecule (or a different type of response from the same molecule). A voltage controller 114 is utilized in a manner similar to that discussed above, to provide voltage inputs to the pairs of SWP and LWP filters forming each of the tunable arrangements, based upon the specific laser wavelength being used as the probe signal. An associated computer processor 116 and a display 118 may also be included and used in a manner similar to that described above to determine changes to the voltages applied to each of the tunable filters in order to provide the desired filter characteristics.

Figure 31:
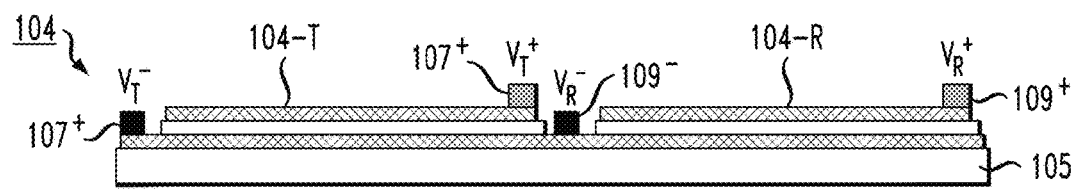
FIG. 31 is a side view of an exemplary tunable dichroic filter for use in Raman spectrometer in accordance with the principles of the present invention.
Figure 32:
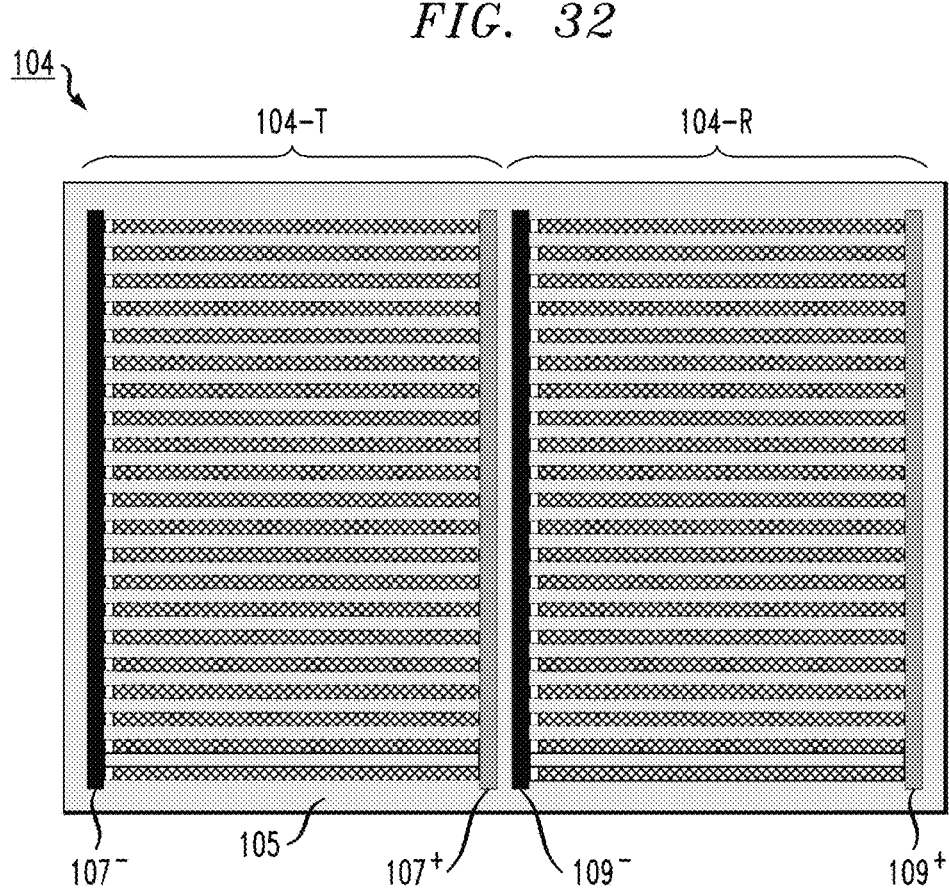
FIG. 32 is a top view of the filter shown in FIG. 31.

FIG. 31 is a side view of an exemplary configuration of a tunable dichroic filter 104 suitable for use in the Raman spectrometer described in association with FIGS. 28 and 30. FIG. 32 is a top view of the same device. As shown, tunable dichroic filter 104 is formed to include a pair of voltage-controlled filters, a transmissive filter 104-T and a reflecting filter 104-R that are preferably formed on the same substrate 105. A pair of voltages VT+ and VT− are applied to conductors 107+ and 107−, respectively, to adjust (tune) the filter response of transmissive filter 104-T. Similarly, a pair of voltages VR+ and VR− are applied to conductors 109+ and 109−, respectively, to adjust (tune) the filter response of reflecting filter 104-R. As with the above-described embodiments, the filter of FIGS. 31 and 32 takes the form of a plasmonic device, which may utilize an array of graphene strips insulated from a lower graphene layer. Alternatively, the dichroic filter may be formed as a tunable LWP filter using (high conductivity) graphene to provide the transmissive and reflective wavelength bands.

Besides its use in the field of spectrometry, the inventive voltage-controlled tunable optical filter is considered to be extremely useful in other imaging types of instrumentation, such as flow cytometry. In particular, flow cytometry is a laser-based (or LED-based) technology employed in cell-based analyses such as counting, sorting, biomarker detection and protein engineering. In use, the cells are suspended in a stream of fluid that is passed through some type of detection apparatus. The "flow" of the cell stream allows for simultaneous multi-parametric analysis of the physical and chemical characteristics of up to thousands of particles per second.

As with fluorescence spectroscopy, a wide range of fluorophores can be used as labels in flow cytometry. Fluorophores, or simply "fluors", are typically attached to an antibody that recognizes a target feature on or in the cell. Each fluorophore has a characteristic peak excitation and emission, where the emission spectra for the various fluors often overlap. Consequently, the combination of labels which can be used depends on the wavelength(s) of sources used to excite the fluorophores and on the detectors available.

Figure 33:
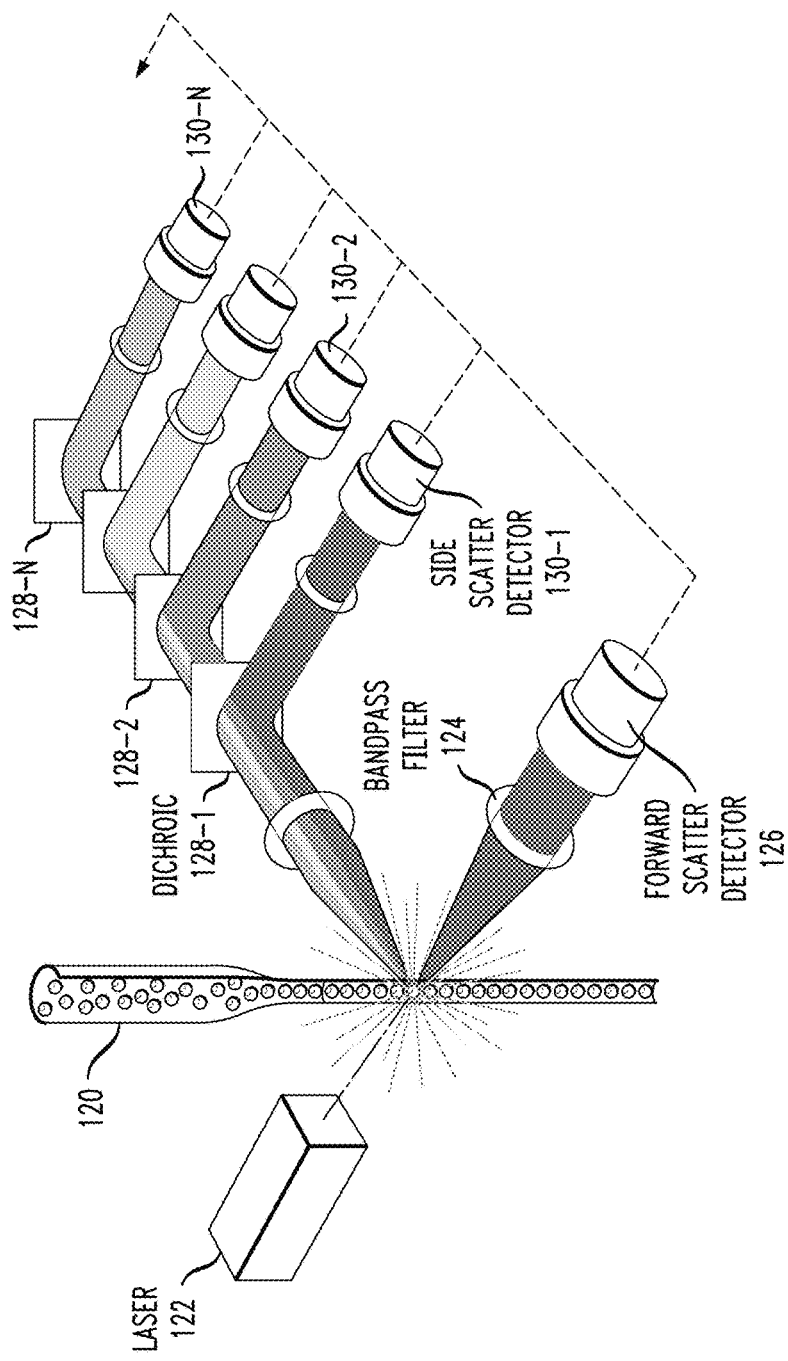
FIG. 33 is a diagram of a conventional prior art flow cytometer.

FIG. 33 is a diagram of a conventional prior art flow cytometer, which is useful in understanding the applicability of the inventive voltage-tunable filter to this type of instrumentation. As shown, a stream of cells 120 is directed through the path of a laser source 122. The result is a separation (scattering) of the various wavelengths, with a first wavelength band passing through a bandpass filter 124 and thereafter directed into a "forward" scatter detector 126. The remaining bands propagate along an orthogonal signal path, passing through a set of dichroic filters 128-1, 128-2, . . . , 128-N that function to separate out a specific wavelength band and direct each band into its own "side" scatter detector 130-1, 130-2, . . . , 130-N, respectively.

Figure 34:
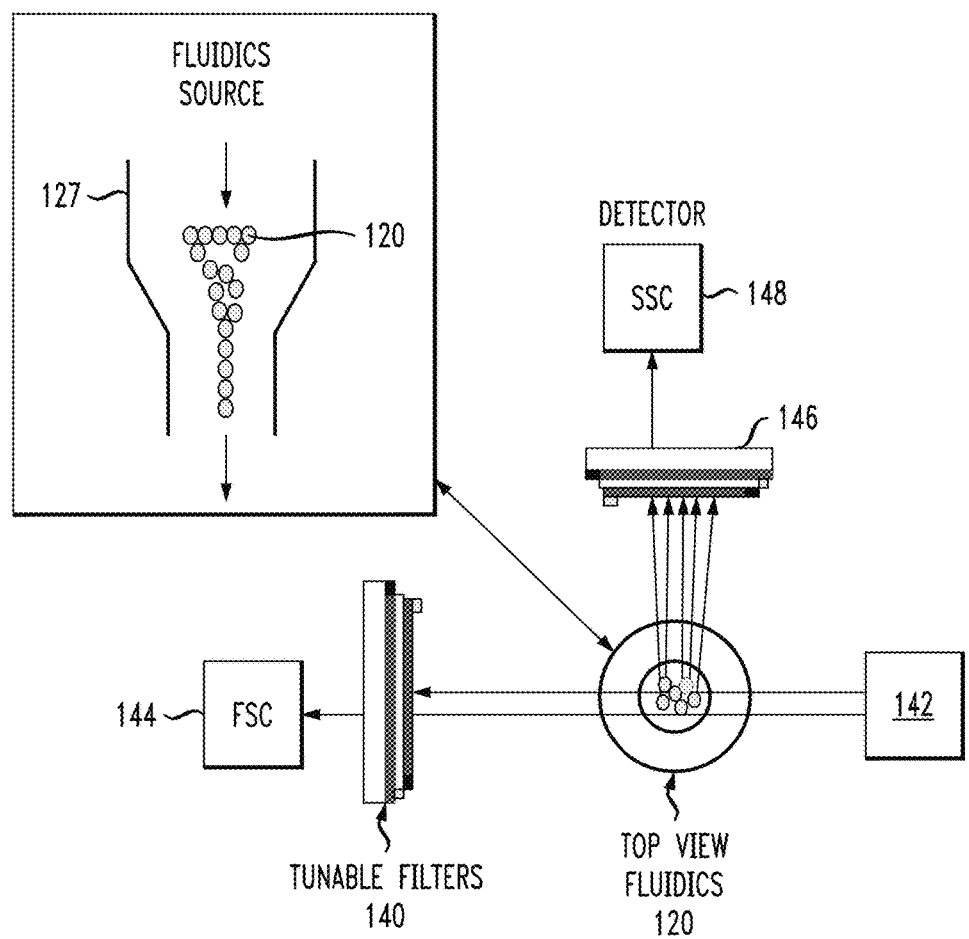
FIG. 34 is a diagram of a flow cytometer including voltage-controlled tunable optical filters formed in accordance with the present invention.

FIG. 34 is a top view of a novel flow cytometer configuration formed in accordance with the present invention where the plurality of dichroic filters is replaced by the utilization of tunable filters. In particular, the "top" of a fluidics source 127 (which allows for a constant stream of cells 120 to pass through the system) is depicted as disposed between laser sources 142 and tunable filters 140. A side view of fluidics source 127 (showing the flow of cells 120) is included as an inset in FIG. 34. As shown, a "forward" tunable filter 140 is disposed in the signal path between a laser source 142 and a forward scatter detector 144. A "side" tunable filter 146 is disposed in the signal path between the portion of the optical signal scattered by the stream of cells 120 and a side scatter detector 148. As with the various embodiments described above, the ability to tune the CWL and BW of the filters provides the ability to tune the specific wavelengths received at forward scatter detector 144 and side scatter detector 148.

FIG. 35 is a diagram of one exemplary embodiment of a flow cytometer formed in accordance with the present invention, based on the diagram shown in FIG. 34. In particular, "forward" tunable filter 140 is defined as an excitation filter, having separately tunable SWP and LWP components. A voltage controller 150 is included in the embodiment and provides the tuning voltage to both devices 140-L and 140-S. Upon encountering the fluid stream, a first wavelength passes through the stream, and is directed through an additional tunable filter 143 (include a SWP filter 143-S and a LWP filter 143-L, with both controlled by voltages from voltage control 150), and thereafter into front scatter detector 144. The remaining wavelengths scatter in the direction of "side" tunable filter 146, again comprising a pair of tunable SWP, LWP filters (shown as 146-S and 146-L, respectively). Voltage controller 150 is used to control the specific wavelength(s) that pass through filter 146, allowing for filter 146 to sweep through a plurality of different wavelength bands and thus utilize a single side scatter detector 148 to collect (as a function of time) the information associated with the plurality of different wavelength bands. The resultant measurements are then passed from voltage controller 150 to computer 152 (and perhaps a display 154) to generate the associated cytometer output results.

While this invention has been described in detail with reference to various preferred embodiments, it should be understood that the invention is certainly not limited to these embodiments, and that various modifications would present themselves to those skilled in the art without departure from the scope and spirit of this invention, as defined by the claims appended hereto.

What is claimed is:

1. An optical-based imaging system including at least one voltage-controlled plasmonic tunable optical filter comprising
    a shortwave pass (SWP) plasmonic filter comprising a plurality of voltage-controlled transparent, conductive strips disposed above and insulated from a layer of transparent, conductive material, the SWP plasmonic filter defined as exhibiting a selected cut-off wavelength $\lambda_S$; and
    a longwave pass (LWP) plasmonic filter comprising a plurality of voltage-controlled transparent, conductive strips disposed above and insulated from a layer of transparent, conductive material, the LWP plasmonic filter defined as exhibiting a selected cut-on wavelength $\lambda_L$, with $\lambda_L$ less than $\lambda_S$, wherein at least one of the SWP plasmonic filter and the LWP plasmonic filter exhibits a voltage-controlled spectral response such that the combination of the SWP and LWP plasmonic filters creates a tunable optical filter defined by the wavelength range between the cut-on wavelength $\lambda_L$ and the cut-off wavelength $\lambda_S$, providing a tunable center wavelength and an independently tunable bandwidth, depending on the selected values for $\lambda_L$ and $\lambda_S$.

2. The optical-based imaging system as defined in claim 1, wherein the imaging system includes an excitation filter for controlling an optical bandwidth used to illuminate a specimen and an emission filter for controlling an optical bandwidth received at a detector from the illuminated specimen, with at least one of the excitation and emission filters formed as a voltage-controlled plasmonic tunable filter.

3. The optical-based imaging system as defined in claim 2 wherein the excitation filter is formed as a voltage-controlled plasmonic tunable excitation filter.

4. The optical-based imaging system as defined in claim 3 wherein the voltage-controlled plasmonic tunable excitation filter is controlled by voltages applied to the SWP and LWP plasmonic filters to create a swept wavelength filter, sweeping across a plurality of different excitation wavelengths.

5. The optical-based imaging system as defined in claim 3 wherein the voltage-controlled plasmonic tunable excitation filter is controlled by voltages applied to the SWP and LWP plasmonic filters to create a blocking filter that prevents excitation wavelengths from passing through, providing a controlled shutter for the imaging system.

6. The optical-based imaging system as defined in claim 3 wherein the imaging system comprises a fluorescence spectrometer and the voltage-controlled plasmonic tunable excitation filter is tunable to excite a plurality of different dyes within a specimen, associated with a plurality of different excitation wavelengths.

7. The optical-based imaging system as defined in claim 3 wherein the imaging system comprises a Raman spectrometer and the voltage-controlled plasmonic tunable excitation filter is tunable to generate vibrational and rotational resonances within an illuminated specimen at a plurality of different excitation wavelengths.

8. The optical-imaging system as defined in claim 3 wherein the imaging system comprises a flow cytometer and the voltage-controlled plasmonic tunable excitation filter is tunable to control a wavelength range directed to a forward-scatter detector of the flow cytometer.

9. The optical-based imaging system as defined in claim 2 wherein the emission filter is formed as a voltage-controlled plasmonic tunable emission filter.

10. The optical-based imaging system as defined in claim 9 wherein the imaging system comprises a fluorescence spectrometer and the voltage-controlled plasmonic tunable emission filter is tunable to maximum signal strength at the associated optical detector.

11. The optical-based imaging system as defined in claim 9 wherein the imaging system comprises a Raman spectrometer and the voltage-controlled plasmonic tunable emission filter is configured as a deep notch filter, centered at the excitation wavelength, to minimize noise at the detector.

12. The optical-based imaging system as defined in claim 9 wherein the imaging system comprises a flow cytometer and the voltage-controlled plasmonic tunable emission filter is configured to sweep across a plurality of side-scattered wavelengths, associated with a plurality of different fluorophores.

13. The optical-based imaging system as defined in claim 2 wherein the optical-based imaging system further comprises a dichroic filter disposed to direct the excitation signal toward the specimen and the emission signal toward the detector, and also maintaining an angular separation between the excitation signal and the emission signal.

14. The optical-based imaging system as defined in claim 13 wherein the dichroic filter comprises a voltage-controlled plasmonic tunable dichroic filter.

15. The optical-based imaging system as defined in claim 13 wherein the voltage-controlled plasmonic tunable dichroic filter is tunable with respect to changes in excitation wavelength.

16. The optical-based imaging system as defined in claim 13 wherein the voltage-controlled plasmonic tunable dichroic filter is tunable with respect to changes in emission wavelength.

17. A voltage-controlled plasmonic tunable optical filter comprising
   a shortwave pass (SWP) plasmonic filter defined as exhibiting a selected cut-off wavelength $\lambda_S$; and
   a longwave pass (LWP) plasmonic filter defined as exhibiting a selected cut-on wavelength $\lambda_L$, with $\lambda_L$ less than $\lambda_S$, wherein at least one of the SWP plasmonic filter and the LWP plasmonic filter exhibits a voltage-controlled spectral response such that the combination of the SWP and LWP plasmonic filters creates a tunable optical filter defined by the wavelength range between the cut-on wavelength $\lambda_L$ and the cut-off wavelength $\lambda_S$, providing a tunable center wavelength and an independently tunable bandwidth, depending on the selected values for $\lambda_L$ and $\lambda_S$, wherein each plasmonic filter comprises a plurality of voltage-controlled transparent, conductive strips disposed above and insulated from a layer of transparent, conductive material, such that the adjustment of a voltage applied to the transparent, conductive strips adjust the spectral response of the associated plasmonic filter.

18. The voltage-controlled plasmonic tunable optical filter as defined in claim 17 wherein the SWP plasmonic filter is formed to exhibit a voltage-controlled spectral response such that the cut-off wavelength $\lambda_S$ is tunable by adjusting a voltage applied thereto.

19. The voltage-controlled plasmonic tunable optical filter as defined in claim 17 wherein the LWP plasmonic filter is formed to exhibit a voltage-controlled spectral response such that the cut-on wavelength $\lambda_L$ is tunable by adjusting a voltage applied thereto.

20. The voltage-controlled plasmonic tunable optical filter as defined in claim 17 wherein the SWP plasmonic filter is formed to exhibit a voltage-controlled spectral response such that the cut-off wavelength $\lambda_S$ is tunable by adjusting a voltage applied thereto and the LWP plasmonic filter is formed to exhibit a voltage-controlled spectral response such that the cut-on wavelength $\lambda_L$ is tunable by adjusting a voltage applied thereto.

21. The voltage-controlled plasmonic tunable optical filter as defined in claim 17 wherein either one or both of the cut-on wavelength $\lambda_L$ and the cut-off wavelength $\lambda_S$ are voltage controlled to create a tunable a center wavelength (CWL) of the optical filter.

22. The voltage-controlled plasmonic tunable optical filter as defined in claim 21 wherein the voltages applied to the SWP and LWP plasmonic filters are controlled in a manner that changes the center wavelength value as a function of time, creating a sweeping filter effect.

23. The voltage-controlled plasmonic tunable optical filter as defined in claim 17 wherein either one or both of the cut-on wavelength $\lambda_L$ and the cut-off wavelength $\lambda_S$ are voltage controlled to provide a tunable a bandwidth (BW) of the optical filter.

24. The voltage-controlled plasmonic tunable optical filter as defined in claim 23 wherein the voltages applied to the SWP and LWP plasmonic filters are controlled in a manner that creates a narrowband filter.

25. The voltage-controlled plasmonic tunable optical filter as defined in claim 17 wherein either one or both of the cut-on wavelength $\lambda_L$ and the cut-off wavelength $\lambda_S$ are voltage controlled to provide both a tunable CWL and a tunable BW of the optical filter, the CWL and BW being independently tunable.

26. The voltage-controlled plasmonic tunable optical filter as defined in claim 17 wherein the voltages applied to the SWP and LWP plasmonic filters are controlled in a manner such that the bandwidth between cut-on wavelength $\lambda_L$ and the cut-off wavelength $\lambda_S$ is essentially zero, preventing light from passing through the filter.

27. The voltage-controlled plasmonic tunable optical filter as defined in claim 17 wherein the transparent, conductive material comprises indium tin oxide (ITO) and the plurality of voltage-controlled transparent, conductive strips comprises a plurality of voltage-controlled strips of ITO.

28. The voltage-controlled plasmonic tunable optical filter as defined in claim 17 wherein the transparent, conductive material comprises graphene and the plurality of voltage-controlled transparent, conductive strips comprises a plurality of voltage-controlled strips of graphene.

29. The voltage-controlled plasmonic tunable filter as defined in claim 17 wherein the filter further comprises a transparent substrate upon which both the SWP plasmonic filter and the LWP plasmonic filter are disposed.

30. The voltage-controlled plasmonic tunable filter as defined in claim 29 wherein the transparent substrate is formed of a flexible polymer.

31. The voltage-controlled plasmonic tunable filter as defined in claim 29 wherein the transparent substrate is formed of a silicon-based material.

32. The voltage-controlled plasmonic tunable filter as defined in claim 29 wherein the transparent substrate is formed of mono- or poly-crystalline CVD diamond.

33. The voltage-controlled plasmonic tunable filter as defined in claim 29 wherein the SWP plasmonic filter and the LWP plasmonic filter are disposed side-by-side on the transparent substrate.

34. The voltage-controlled plasmonic tunable filter as defined in claim 29 wherein the SWP plasmonic filter and the LWP plasmonic filter are disposed in a stacked configuration on the transparent substrate, with an insulating layer included between the stacked configuration of plasmonic filters.

35. The voltage-controlled plasmonic tunable filter as defined in claim 17 wherein the filter further comprises a first transparent substrate upon which the SWP plasmonic filter is disposed and a second transparent substrate upon which the LWP plasmonic filter is disposed.

36. The voltage-controlled plasmonic tunable filter as defined in claim 17 wherein each strip of the plurality of transparent, conductive strips is configured as a quantum dot chain that reduces polarization sensitivity of the plasmonic tunable filter.

37. The voltage-controlled plasmonic tunable filter as defined in claim 36 wherein each quantum dot chain comprises a plurality of connected quantum rectangles.

38. The voltage-controlled plasmonic tunable filter as defined in claim 36 wherein each quantum dot chain comprises a plurality of connected quantum circles.

* * * * *